(12) United States Patent
Schumacher et al.

(10) Patent No.: US 11,883,078 B2
(45) Date of Patent: *Jan. 30, 2024

(54) JOINT FUSION IMPLANT AND METHODS

(71) Applicants: IMDS LLC, Providence, UT (US); Mayo Foundation for Medical Education and Research, Rochester, MN (US)

(72) Inventors: Brian Scott Schumacher, Orlando, FL (US); Nicholas Slater, Chandler, AZ (US); William W. Cross, III, Rochester, MN (US)

(73) Assignees: IMDS LLC, Providence, UT (US); Mayo Foundation for Medical Education and Research, Rochester, MN (US)

( * ) Notice: Subject to any disclaimer, the term of this patent is extended or adjusted under 35 U.S.C. 154(b) by 319 days.

This patent is subject to a terminal disclaimer.

(21) Appl. No.: 17/473,997

(22) Filed: Sep. 13, 2021

(65) Prior Publication Data
US 2021/0401472 A1 Dec. 30, 2021

Related U.S. Application Data

(63) Continuation of application No. 16/528,591, filed on Jul. 31, 2019, now Pat. No. 11,129,649, which is a
(Continued)

(51) Int. Cl.
*A61B 17/70* (2006.01)
*A61B 17/88* (2006.01)
(Continued)

(52) U.S. Cl.
CPC ...... *A61B 17/7055* (2013.01); *A61B 17/1617* (2013.01); *A61B 17/1671* (2013.01);
(Continued)

(58) Field of Classification Search
CPC ............ A61B 17/7055; A61B 17/1617; A61B 17/8625
See application file for complete search history.

(56) References Cited

U.S. PATENT DOCUMENTS 9,119,678 B2 * 9/2015 Duggal .............. A61B 17/8695
10,136,929 B2 * 11/2018 Fallin ................. A61B 17/1725
(Continued)

*Primary Examiner* — Christian A Sevilla
(74) *Attorney, Agent, or Firm* — David Meibos; Maywood IP Law

(57) ABSTRACT

An implant for fusing a joint between first and second bone portions. The implant includes a screw member, and a washer polyaxially rotatable relative to the screw member. The screw member includes a head, a lag zone, and a threaded engagement zone. The implant includes a fusion zone for joint compression, extending from the washer to the proximal end of the engagement zone. Fenestrations may be present in the fusion zone. The length of the fusion zone ranges from about 10 mm to about 37 mm. Different surface finishes including roughened and non-roughened may be applied selectively to selected portions of the implant. In an embodiment, the joint is a sacro-iliac joint, and upon implantation the implant extends from the exterior of the ilium, across the joint and into the sacral vertebral body. Instrumentation and methods for preparing the joint and implanting the implant are disclosed.

7 Claims, 23 Drawing Sheets

Related U.S. Application Data continuation of application No. 15/420,849, filed on Jan. 31, 2017, now Pat. No. 10,413,332, which is a continuation-in-part of application No. 15/137,848, filed on Apr. 25, 2016, now Pat. No. 9,833,321, and a continuation-in-part of application No. 15/137,804, filed on Apr. 25, 2016, now Pat. No. 10,751,071.

(51) Int. Cl.
*A61B 17/86* (2006.01)
*A61B 17/16* (2006.01)
*A61B 17/00* (2006.01)

(52) U.S. Cl.
CPC ............ *A61B 17/86* (2013.01); *A61B 17/863* (2013.01); *A61B 17/864* (2013.01); *A61B 17/8625* (2013.01); *A61B 17/8695* (2013.01); *A61B 17/8811* (2013.01); *A61B 2017/0046* (2013.01)

(56) References Cited

U.S. PATENT DOCUMENTS

| | | | |
|---|---|---|---|
| 2002/0198527 A1* | 12/2002 | Muckter | A61B 17/866 606/907 |
| 2011/0166575 A1* | 7/2011 | Assell | A61B 17/32002 606/79 |
| 2016/0038201 A1* | 2/2016 | Cummings | A61B 17/8875 606/304 |
| 2017/0112552 A1* | 4/2017 | Sinnott | A61B 17/863 |

* cited by examiner

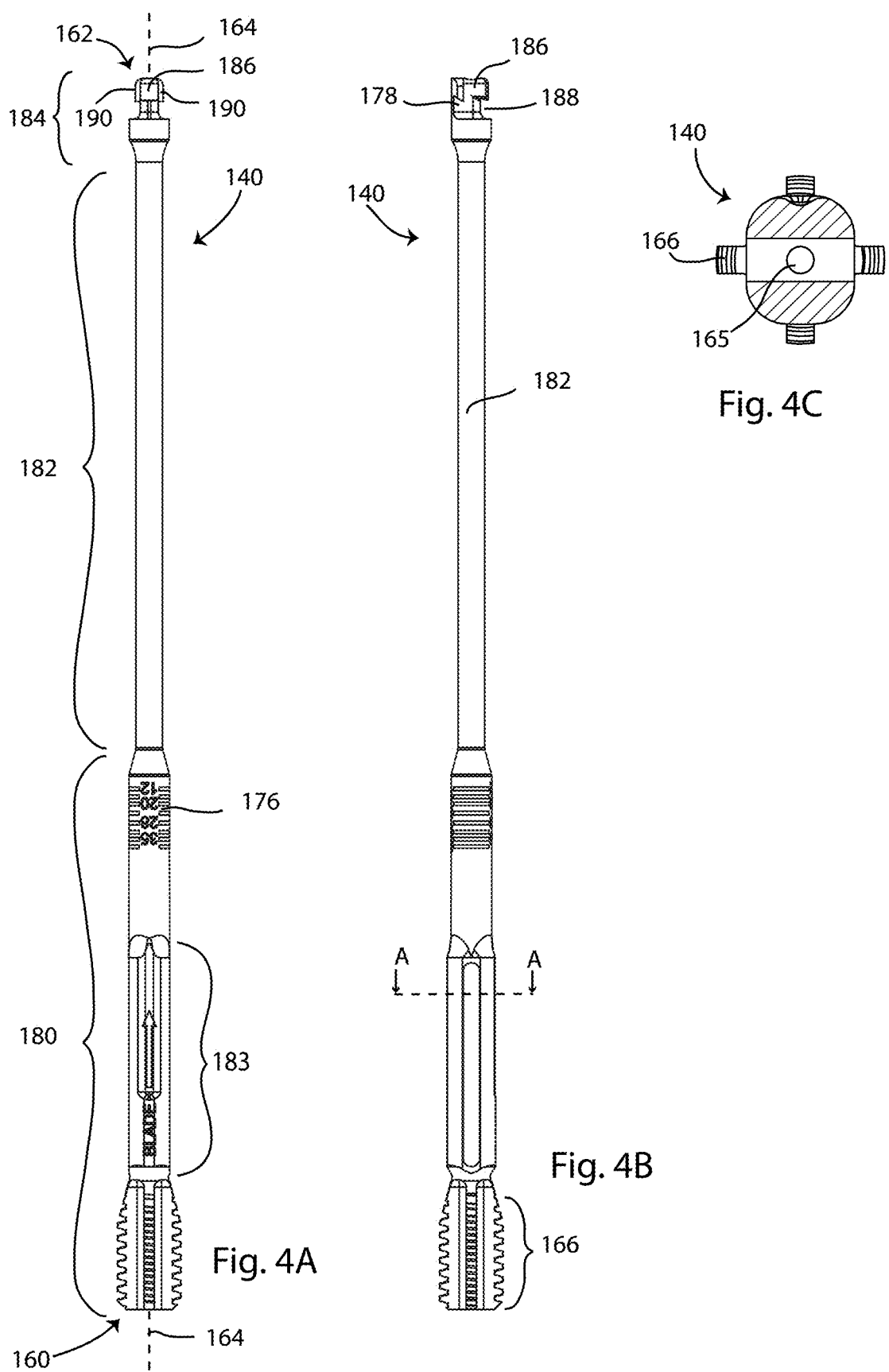

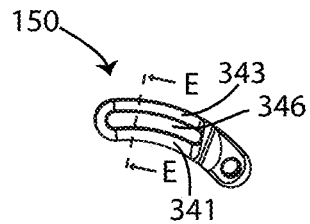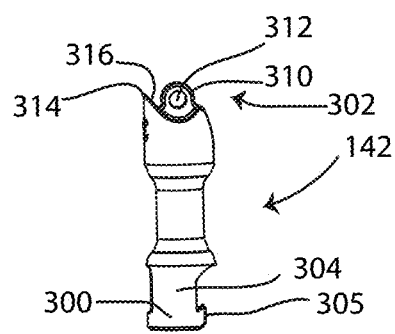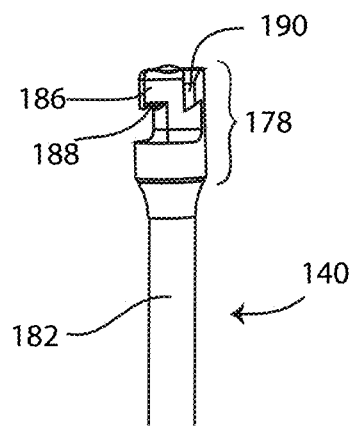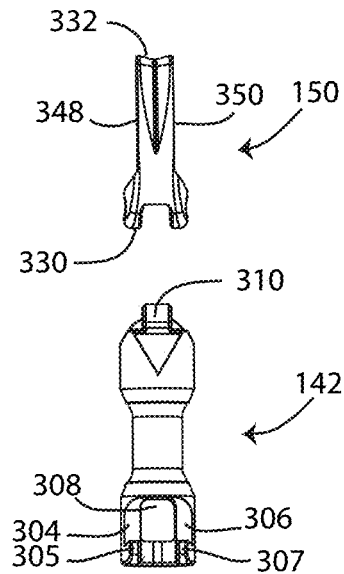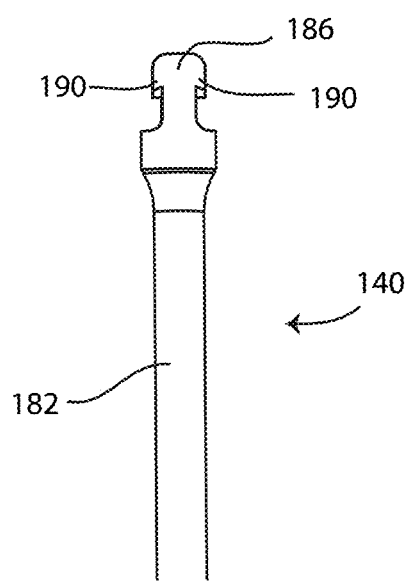
Fig. 5A　　　　　　　　　　Fig. 5B

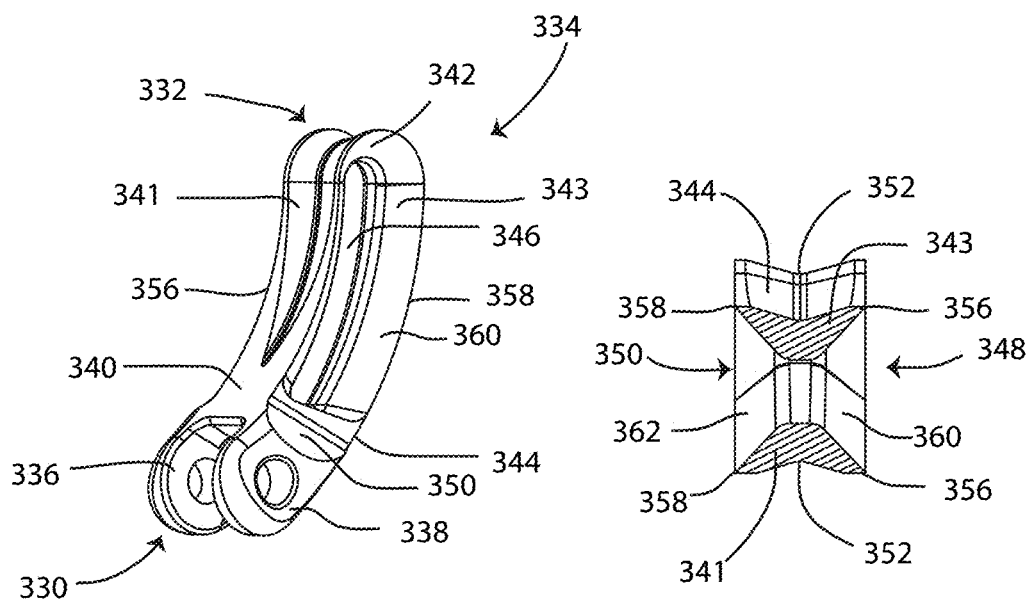
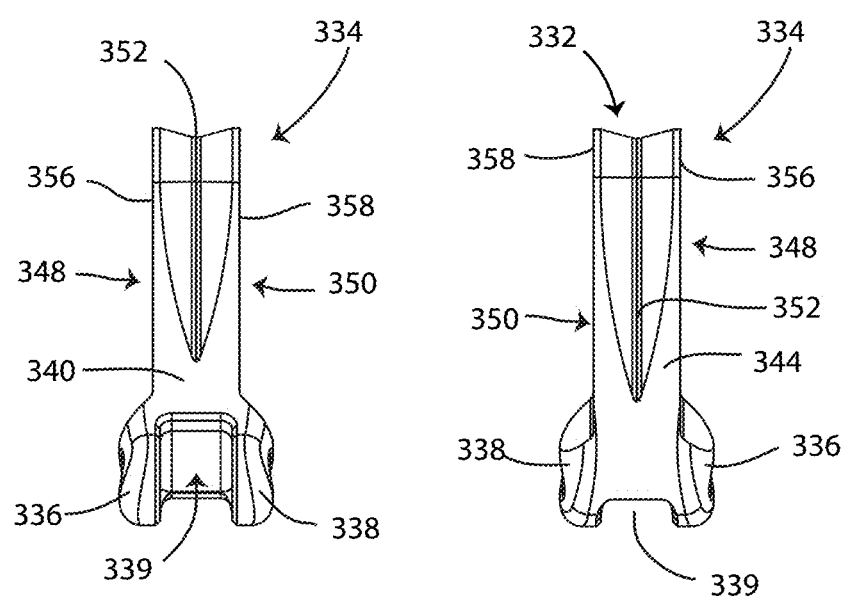

JOINT FUSION IMPLANT AND METHODS

CROSS-REFERENCE TO RELATED APPLICATIONS

This application is a continuation of U.S. patent application Ser. No. 16/528,591 filed on Jul. 31, 2019, entitled JOINT FUSION IMPLANT AND METHODS, which is a continuation of U.S. patent application Ser. No. 15/420,849 filed on Jan. 31, 2017, entitled JOINT FUSION IMPLANT AND METHODS, which issued on Sep. 17, 2019 as U.S. Pat. No. 10,413,332.

U.S. patent application Ser. No. 15/420,849 is a continuation-in-part of U.S. patent application Ser. No. 15/137,804 filed on Apr. 25, 2016, entitled JOINT FUSION INSTRUMENTATION AND METHODS, which issued on Aug. 25, 2020 as U.S. Pat. No. 10,751,071 and U.S. patent application Ser. No. 15/137,848 filed on Apr. 25, 2016, entitled JOINT FUSION INSTRUMENTATION AND METHODS, which issued on Dec. 5, 2017 as U.S. Pat. No. 9,833,321. The foregoing are incorporated herein by reference as though set forth in their entirety.

STATEMENT REGARDING PRIOR DISCLOSURES BY THE INVENTOR OR A JOINT INVENTOR

William W. Cross III is the inventor of the subject matter of U.S. patent application Ser. No. 14/790,480, filed on Jul. 2, 2015 and entitled SACROILIAC JOINT FUSION SCREW AND METHOD, published as U.S. Patent Application Publication no. US2016/0000488A1. William W. Cross III is an inventor of the subject matter of the present disclosure. The above-identified patent application publication is incorporated herein by reference.

BACKGROUND OF THE INVENTION

The present invention relates to implants and methods for joint fusion. More specifically, the invention relates to implants, instrumentation and methods for fusing a sacroiliac joint.

The sacroiliac (SI) joints are formed by the connection of the sacrum and the right and left iliac bones. While most of the spinal vertebrae are mobile, the sacrum is made up of five vertebrae that are fused together and do not move. The iliac bones are the two large bones that make up the pelvis. As a result, the SI joints connect the spine to the pelvis, and form the largest axial joints in the body. The sacrum and the iliac bones are held together and supported by a complex collection of strong ligaments. There is relatively little motion at the SI joints; there are normally less than 4 degrees of rotation and 2 mm of translation at these joints. Most of the motion in the area of the pelvis occurs either at the hips or the lumbar spine. These joints support the entire weight of the upper body when it is erect, placing a large amount of stress across them. This can lead to wearing of the cartilage of the SI joints. Some causes of degeneration and/or pain in the SI joints include osteoarthritis, pregnancy, leg length discrepancy, gout, rheumatoid arthritis, psoriatic arthritis, reactive arthritis, and ankylosing spondylitis.

Treatment options have been limited to conservative care involving physical therapy and joint injections or traditional open SI joint arthrodesis surgery until recently. Open arthrodesis procedures reported in the literature require relatively large incisions, significant bone harvesting, and lengthy hospital stays; moreover, they may require non-weight bearing for several months.

The systems and methods for sacroiliac joint fusion disclosed here can be used to provide SI joint arthrodesis in a minimally invasive procedure. SI joint fusion using the systems and methods disclosed herein may provide advantages which can include a small incision, relatively short operating time with fewer steps, minimal blood loss, and a relatively short period of postoperative immobilization. For example, the steps disclosed herein for creating a cavity in the joint, filling it with graft material, and inserting a fusion device, may all be accomplished through a single access cannula in a single procedure. The size and configuration of the cutting instrument allows insertion into a bone or joint through a relatively narrow pathway, and creation of an undercut cavity within the bone or joint. Due to the shape and rigid construction of the blade disclosed herein and its assembly within the cutting instrument, the bone cutting instrument disclosed herein may create a cleaner cavity in a relatively short time, without the need to switch out blade members or employ multiple cutting instruments. Implants for joint fusion are disclosed herein, including an embodiment for SI joint fusion having a design which is based on specific anatomical measurements of the ilium, sacrum, and SI joint space. An embodiment of the implant includes a fusion zone specifically sized to span the SI joint and provide compression for long-term joint fixation, and a threaded engagement zone specifically sized to extend to and anchor in the body of the sacral vertebra.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 4A is a front view of a blade shaft of the cutter of FIG. 2A; FIG. 4B is a side view of the blade shaft of FIG. 4A; FIG. 4C is a cross-sectional view of the blade shaft of FIG. 4B, taken along line A-A in FIG. 4B;

FIG. 5A is a partially exploded side view of one end of a blade shaft assembly for the cutter of FIG. 2A, the assembly having a blade shaft, a blade holder, and a blade; FIG. 5B is a partially exploded back view of the blade shaft assembly of FIG. 5A;

FIG. 6A is a perspective view of the blade of FIG. 5A; FIG. 6B is a front view of the blade of FIG. 5A; FIG. 6C is a back view of the blade of FIG. 5A; FIG. 6D is a cross-sectional view of the blade of FIG. 5A taken along line E-E of FIG. 5A;

in FIGS. 10-22 the first and second bones and the joint are depicted in cross-section in order to view the components of the invention in situ;

FIG. 11 is a view of the guide wire and dilators of FIG. 10, with a cannula inserted over the guide wire and dilators and docked into the first bone;

FIG. 12 is a view of the cannula of FIG. 11, with an impactor mounted on an end of the cannula;

FIG. 13 is a view of the cannula of FIG. 11, with an support struts attached to the cannula;

FIG. 15 is a view of the cannula and sleeve of FIG. 14A, with a drill inserted through the cannula and sleeve, and a passageway drilled across the joint;

FIG. 17 is a view of the cannula, sleeve and cavity of FIG. 16A, with a suction tool inserted through the cannula and sleeve and into the cavity;

FIG. 18 is a view of the cannula, sleeve and cavity of FIG. 16A, with a graft funnel mounted in the cannula, a tamp inserted through the graft funnel, and bone graft material in the cavity;

FIG. 19 is a view of the cannula, sleeve, cavity and bone graft material of FIG. 18, with a drill inserted through the cannula and sleeve, and another passageway drilled across the joint deeper into the second bone;

FIG. 20 is a view of the cannula, sleeve, cavity, bone graft material and passageway of FIG. 19, with a guide wire installed though the passageway and into the second bone and a length gauge mounted on the cannula;

FIG. 21 is a view of the cannula, sleeve, cavity, bone graft material, guide wire passageway and of FIG. 19, with the fusion device of FIG. 1 implanted in the first bone and second bone, across the joint;

FIG. 22 is a view of the joint and fusion device of FIG. 21, with a guide brace mounted over the guide wire and the supplementary screw inserted in the first bone and second bone, across the joint;

DETAILED DESCRIPTION OF THE EMBODIMENTS

Figure 1:
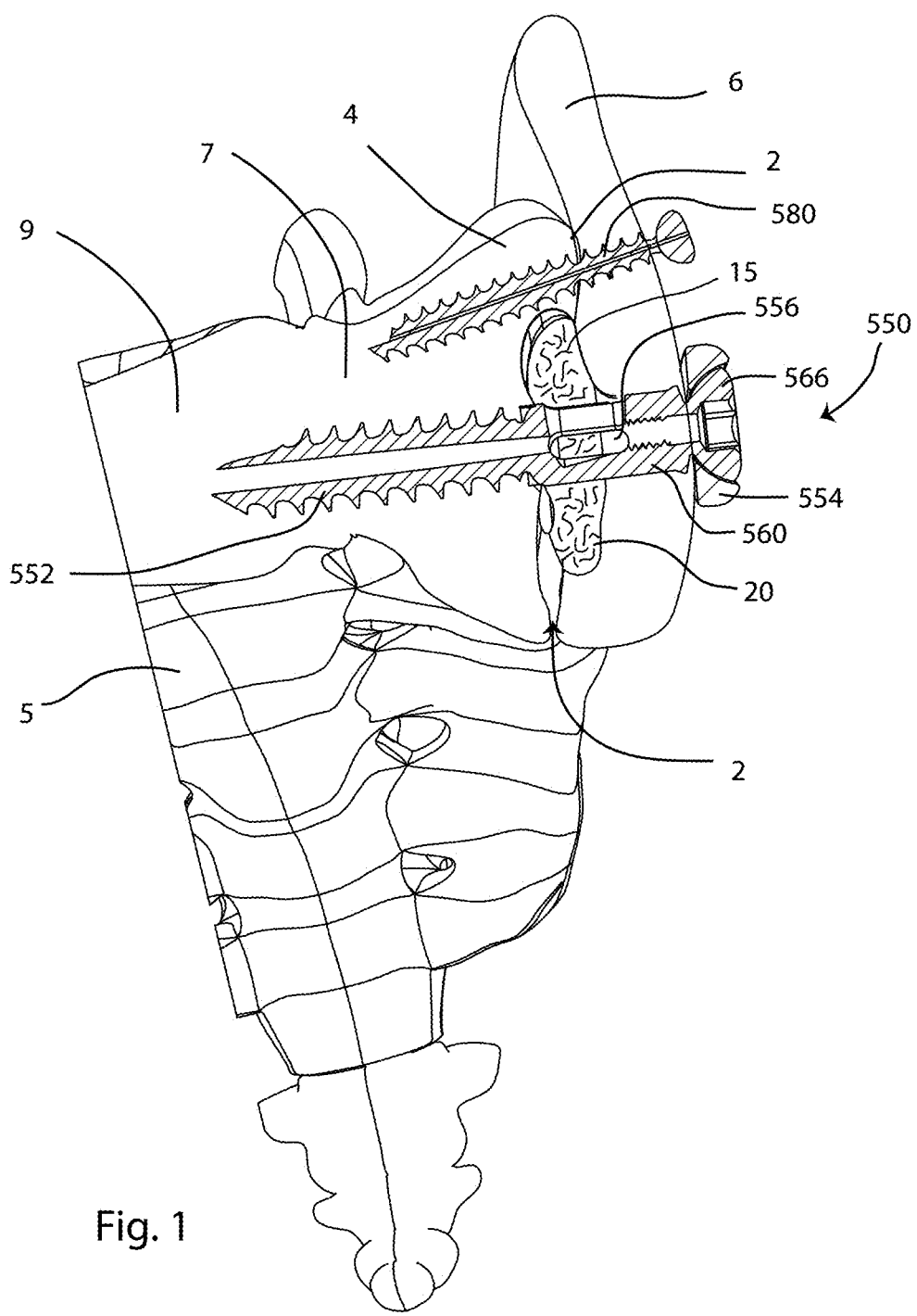
FIG. 1 illustrates a cross-sectional view of a natural sacroiliac joint and a cavity extending across the joint, the cavity filled with bone graft material, and the joint fused by a fusion device comprising a screw member and a washer, and a supplementary screw.

The present invention relates specifically to systems and methods for fusion of a sacroiliac joint, and more generally to systems and methods for creating a cavity in a bone or joint. Those of skill in the art will recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

The terms "front", "side", "back", "upper" and "lower" are used herein to identify a relative frame of reference to a particular device or an individual element of a device. In alternate embodiments the front or upper side of a device or element may be established on any desired side of the device or element.

According to a first aspect of the disclosure, an implant for providing compression across a joint between a first bone portion and a second bone portion, wherein a cavity is located within the joint between the first bone portion and the second bone portion, comprises: a screw member having a screw head, and a screw body projecting distally from the screw head along a longitudinal axis to a screw distal end, the screw body comprising a non-threaded lag zone and a threaded engagement zone, the lag zone extending from the screw head distally to the engagement zone, the engagement zone extending from the lag zone to the screw distal end; and a washer member having a proximal side and a distal side, and a bore having a central bore axis; wherein the screw head is received in the washer member, and the screw body projects distally from the washer member; and an implant fusion zone having a length which is measured from the distal side of the washer member to a proximal end of the screw engagement zone, wherein the length of the implant fusion zone ranges from about 10 mm to about 37 mm.

Embodiments of this aspect of the disclosure may include one or more of the following features: The washer member further includes a semispherical capsule between the proximal side and the distal side, and the screw head is received in the semispherical capsule to permit polyaxial angulation of the washer member with respect to the screw member. The permitted polyaxial angulation of the washer member central bore axis with respect to the screw member longitudinal axis ranges from at least −8 degrees to at least +8 degrees. An annular groove is formed between the screw head and the screw body, wherein the screw is smaller in diameter at the annular groove than at the lag zone or at the screw head. The washer member is captive to the screw member. The screw member comprises a central longitudinal bore extending from the screw head to the screw distal end. The lag zone includes at least one fenestration which opens into the central longitudinal bore. At least a portion of the fenestration is located within the implant fusion zone. An overall length of the implant, measured from the distal side of the washer to the screw distal end when the washer central bore axis is coaxial with the screw member longitudinal axis, ranges from about 40 mm to about 110 mm. The implant comprises at least two different surface finishes. The lag zone and at least a portion of the threaded engagement zone comprise a roughened surface finish; the distal end of the screw member comprises a non-roughened surface finish; and the screw head and washer semispherical capsule comprise a non-roughened surface finish. The implant is a sacro-ilial fusion implant, wherein the joint is a sacroiliac joint, the first bone portion is an ilium, the second bone portion is a sacrum, and the cavity is located between the ilium and the sacrum; wherein, when the implant is installed across the sacroiliac joint, the distal side of the washer member is in contact with an exterior surface of the ilium, the implant fusion zone extends at least partially across the sacroiliac joint and the cavity, and the threaded engagement zone is at least partially embedded in the sacrum.

According to a second aspect of the disclosure, a method for compressing a joint between a first bone portion and a second bone portion, wherein a cavity is located within the joint between the first bone portion and the second bone portion, comprises providing an implant comprising a screw member having a screw head and a screw body projecting distally from the screw head along a longitudinal axis to a screw distal end, the screw body comprising a non-threaded lag zone and a threaded engagement zone; and a washer member having a proximal side and a distal side, wherein the screw head is received in the washer member; wherein the implant further comprises a fusion zone having a length which is measured from the distal side of the washer member to a proximal end of the screw engagement zone, wherein the length of the implant fusion zone ranges from about 10 mm to about 26 mm; inserting the screw body engagement zone through the first bone portion and into the cavity; engaging the screw body engagement zone with the second bone portion; positioning at least a portion of the lag zone within the cavity; rotating the screw member to compress the joint; and angling the washer member with respect to the screw member to permit maximum surface contact of the distal side of the washer member with the first bone portion.

Embodiments of this aspect of the disclosure may include one or more of the following features and/or methods: The lag zone comprises a fenestration opening into a central longitudinal bore, and the method further comprises filling the fenestration with bone graft material. Filling the cavity with bone graft material. The washer member comprises a bore having a central bore axis. Angling the washer member with respect to the screw member comprises angling the washer member central bore axis with respect to the screw member longitudinal axis within the range of at least −8 degrees to at least +8 degrees. The implant is a sacro-ilial fusion implant and the joint is a sacro-iliac joint, and wherein the first bone portion is an ilium, and the second bone portion is a sacrum, and the cavity is located between the ilium and the sacrum. Positioning the fusion zone to extend into cavity, wherein the fusion zone crosses the first bone portion and extends into cavity. Positioning the fusion zone to contact the second bone portion.

According to a third aspect of the disclosure, a system for compressing a joint between a first bone portion and a second bone portion comprises an instrument for excising a cavity between the first bone portion and the second bone portion, the instrument having a handle and a blade assembly, wherein the blade assembly is movable between a retracted configuration and an extended configuration relative to an instrument longitudinal axis to define a cutting radius; and an implant for providing compression across the first bone portion, the cavity, and the second bone portion to fuse the joint, wherein the implant comprises: a screw member having a screw head, and a screw body projecting distally from the screw head along a longitudinal axis to a screw distal end, the screw body comprising a lag zone and a threaded engagement zone; a washer member having a proximal side and a distal side, wherein the screw head is received in the washer member, and the screw body projects distally from the washer member; and an implant fusion zone is defined to extend from the distal side of the washer member to a proximal end of the screw threaded engagement zone.

Embodiments of this aspect of the disclosure may include one or more of the following features: The lag zone is non-threaded and extends from the screw head distally to the engagement zone, and the engagement zone extends distally from the lag zone to the screw distal end. The screw body comprises a central longitudinal bore extending from the screw head to the screw distal end, and the lag zone comprises a fenestration opening into the central longitudinal bore. The washer member comprises a semispherical capsule between the proximal side and the distal side, and the screw head is received in the semispherical capsule to permit polyaxial angulation of the washer member with respect to the screw member. The washer comprises a bore having a central bore axis, wherein the permitted polyaxial rotation angulation of the washer member central bore axis with respect to the screw member longitudinal axis ranges from at least −8 degrees to at least +8 degrees. An overall length of the implant, measured from the distal side of the washer to the screw distal end when the washer central bore axis is coaxial with the screw member longitudinal axis, ranges from about 40 mm to about 110 mm. The length of the implant fusion zone ranges from about 10 mm to about 37 mm. The implant is a sacro-ilial fusion implant, and the joint is a sacroiliac joint, the first bone portion is an ilium, the second bone portion is a sacrum, and the cavity is excised between the ilium and the sacrum. When the implant is installed across the sacroiliac joint, the distal side of the washer member is in contact with an exterior surface of the ilium, the implant fusion zone extends at least partially across the sacroiliac joint and the cavity, and the threaded engagement zone is embedded in the sacrum. An outer diameter of the cavity is determined by the instrument cutting radius, and the maximum outer diameter of the implant is less than the cavity outer diameter.

FIG. 1 illustrates a natural sacroiliac joint fused by methods of the invention. The sacroiliac joint 2 comprises the meeting of a sacrum 5 and an ilium 6. According to methods of the invention disclosed herein, a cavity 20 is created between the sacrum 5 and the ilium 6, and may be filled with bone graft material 15. A fusion device 550 is implanted across the joint 2 to provide compression and fuse the joint. The fusion device may be sized to extend through the ilium 6, across the joint 2 and cavity 20, and into the sacrum 5, extending through the cortical bone 4, the sacral ala 7, and into the sacral vertebrae 9 of the sacrum 5. It is appreciated that the instrumentation and methods disclosed herein may also be applied to provide fusion in any other joint, or to provide fusion between two or more bones or bone portions.

FIGS. 2-9B disclose a cutting instrument, herein referred to as a cutter 100, which may be used to create the cavity 20 in the joint 2. In other embodiments of the method, cutter 100 may applied to create a cavity within a bone or bones, and/or across a joint. Referring to FIGS. 2A-2C, cutter 100 outwardly comprises a handle portion 102, a shaft portion 104, and a blade portion 106. In use by a practitioner, the handle portion 102 may be gripped and moved to direct the shaft and blade portions 104, 106 to a specific area such as a bone or joint, and manipulated to deploy a blade to create a cavity in the bone or joint. The cutter comprises a proximal end 110 and a distal end 112 with a cutter central longitudinal axis 114 extending therebetween.

Figure 2A:
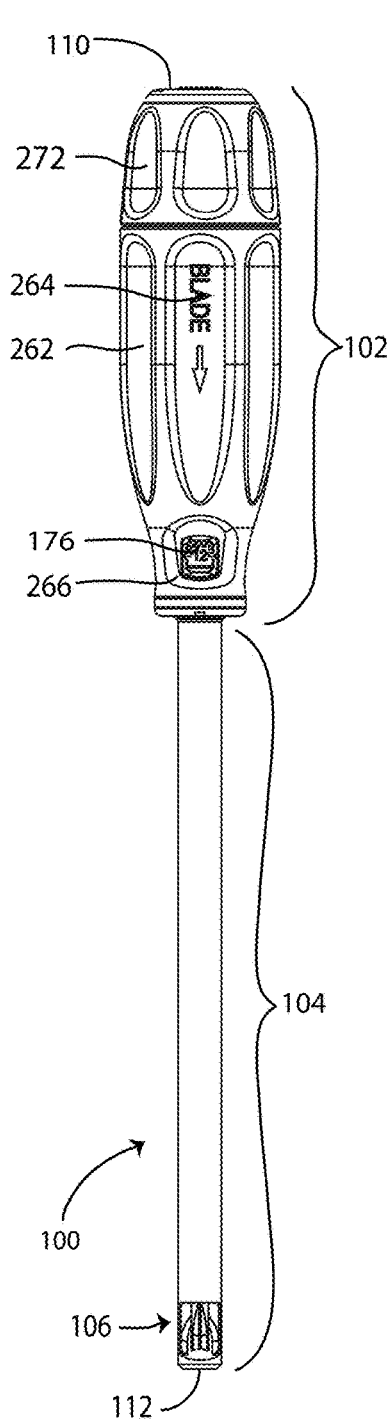
FIG. 2A illustrates a front view of a cutter which may be used to create the cavity of FIG. 1, the cutter having a blade in a retracted configuration.
Figure 2B:
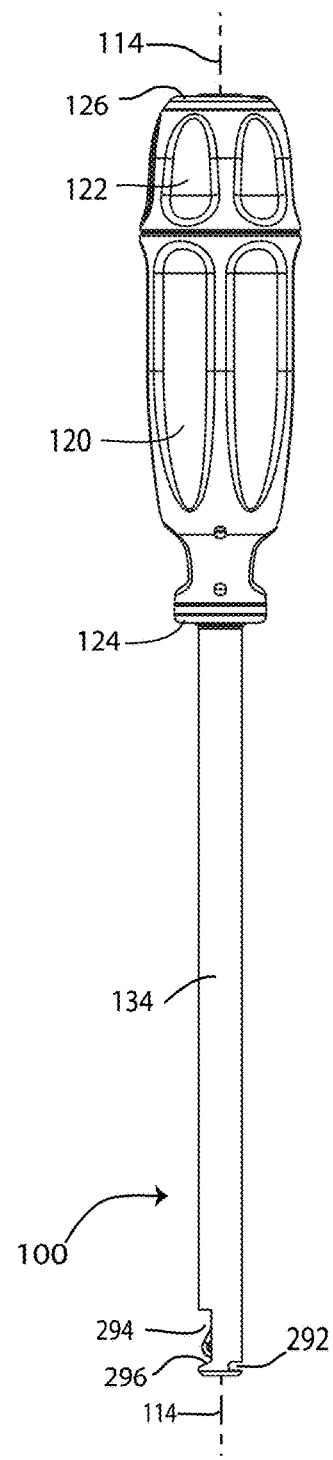
FIG. 2B is a side view of the cutter of FIG. 2A, the side view rotated 90 degrees from the front view.
Figure 2C:
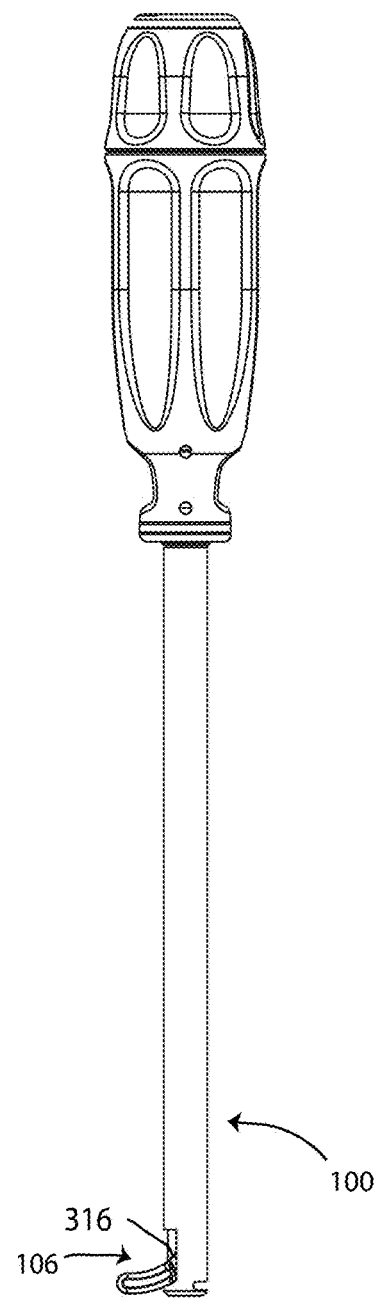
FIG. 2C is a side view of the cutter of FIG. 2A, with the blade in an extended configuration.
Figure 3:
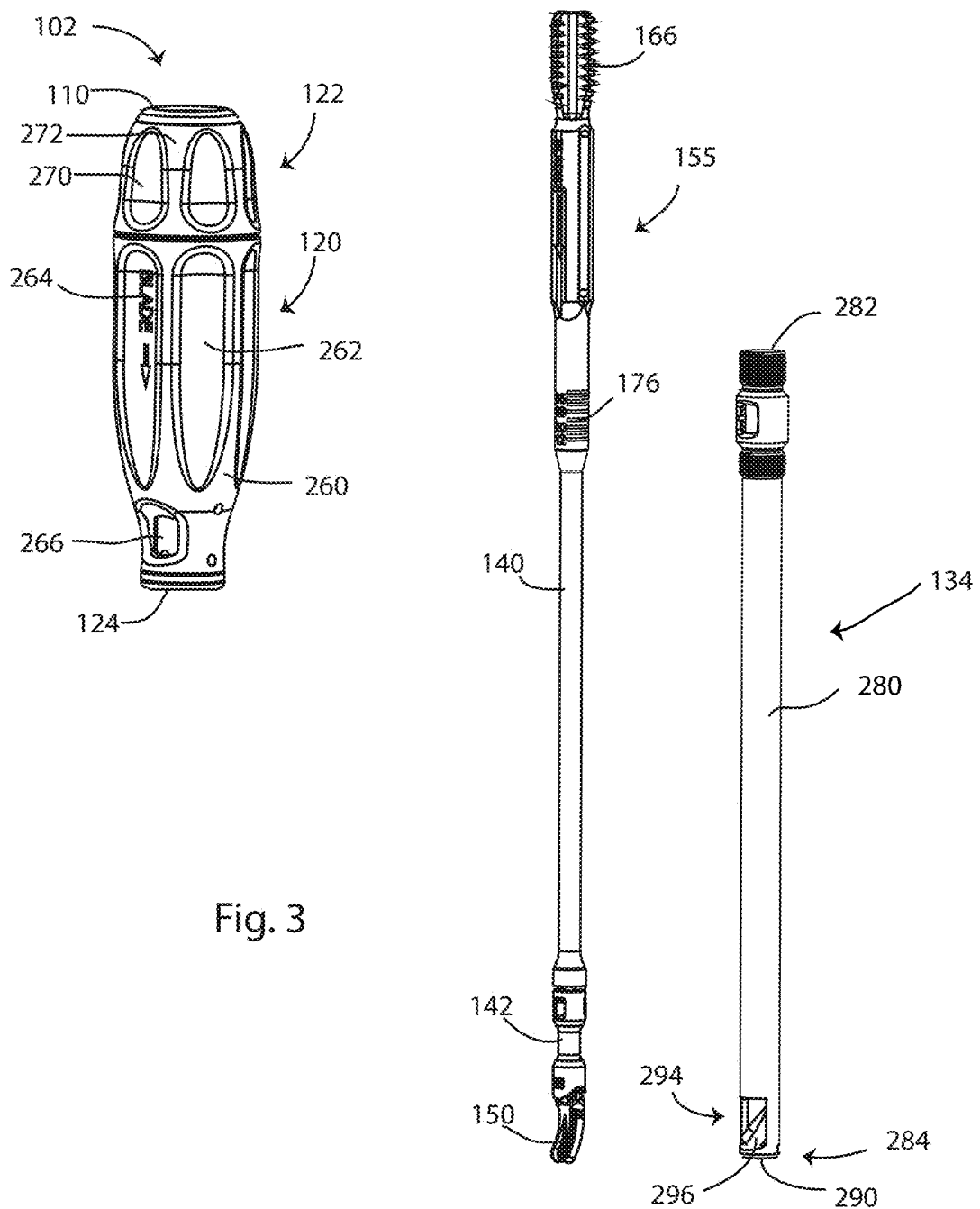
FIG. 3 is a partially exploded view of the cutter of FIG. 2A, the cutter including a handle assembly, a blade assembly, and an outer tube.

Referring to FIGS. 2A-3, the handle portion 102 comprises a handle 120 and a knob 122, and has a distal end 124 and a proximal end 126. The shaft portion 104 comprises an outer tubular member or outer tube 134 which extends distally from the handle portion 102 and terminates at the distal end 112. Housed within the outer tube 134, and handle 120 is a blade shaft 140. The blade shaft 140 extends from the proximal end 110 of the cutter, through the knob 122, handle 120 and outer tube 134. At a distal end of the blade shaft 140, a blade 150 is modularly and pivotably connected to the blade shaft 140 via a blade retainer 142. The blade may also be referred to as a cutting member, or a decorticator. In alternative embodiments, the blade may be monolithic with the blade shaft or may be permanently attached to the blade shaft.

Referring to FIG. 2A, handle 120 includes a handle outer surface 260 which can include gripping features 262 and indicia 264. Indicator windows 266 allow viewing of markings 176 from either side of the handle 120. Similarly, the knob 122 includes a knob outer surface 270 which can include gripping features 272 and indicia.

Referring to FIGS. 4A, 4B and 4C, additional detail of the blade shaft 140 is shown. Blade shaft 140 extends between a proximal end 160 and a distal end 162 along a shaft central longitudinal axis 164. When the blade shaft 140 is assembled with the outer tube and handle, the shaft central longitudinal axis 164 is coaxial with the cutter central longitudinal axis 114. In an embodiment, the blade shaft 140 may be cannulated throughout, having a central bore 165. The blade shaft can include a proximal handle portion 180, a shaft 182, and a distal attachment portion 184. The blade shaft may include an engagement feature 166 which engages with the knob 122, forming an actuation mechanism which controls extension and retraction of the blade 150.

As seen in FIGS. 4A and 4C, the handle portion 180 of the blade shaft 140 includes a longitudinal section 183 which is generally rectangular in cross-section. The rectangular section engages with the handle 120 to prevent rotation of the blade shaft 140 relative to the handle 120. Indicia, which may take the form of the markings 176, are present on the blade shaft and positioned to be visible through a window in the handle 120, allowing a practitioner to determine the diameter of the cavity being excised by the blade 150. At the distal end 162 of the blade shaft 140, an attachment feature 178 protrudes distally allowing for attachment of the blade holder 142. The attachment feature 178 is shaped as a boss 186 having an undercut 188 and paired angled projections or ears 190 to retain the blade holder 142. In another embodiment, the blade holder may connect to the blade shaft in another connection mechanism, or may be permanently connected. In another embodiment, the blade 150 may be directly connected to the blade shaft 140.

With reference to FIGS. 2A and 3, outer tube 134 includes a tubular body 280 extending between a proximal end 282 and a distal end 284. The distal end 284 of the tubular body 280 terminates in a distal end face 290. Adjacent the distal end 284 is a notch 292 which may be viewed fluoroscopically to ascertain the position of the distal end 112 of the cutter 100 during a procedure. A blade window 294 functions as an opening to allow the blade 150 to protrude out of the tubular member for cutting procedures. A ramped surface 296 opposite and interior to the blade window 294 guides the blade 150 as it is urged out of the window 294, guiding the blade to project laterally relative to the cutter axis 114. When the blade 150 is fully projected away from the cutter longitudinal axis 114 and out the window 294, the ramped surface 296 functions as a stop to prevent further distal movement of the blade 150 and hold it rigid relative to the cutter 100.

The connections between the blade shaft 140, blade holder 142 and blade 150 are illustrated in FIGS. 5A and 5B. In the embodiment depicted, blade holder 142 may be snapped on and off of blade shaft 140. Blade holder 142 includes a first or shaft end 300 and a second or blade end 302. The shaft end 300 is U-shaped, comprising a pair of connected sidewalls 304, 306 separated by a gap 308 shaped to receive the blade shaft boss 186. Each sidewall terminates in a tab 305, 307. When the blade holder is snapped on to the blade shaft 140, the boss 186 is received in the gap 308, and tabs 305, 307 are engaged under the angled projections, or ears, 190.

The blade end 302 includes a receiver boss 310 having a bore 312, the bore extending perpendicular to the longitudinal axis of the blade holder 142. The blade end 302 terminates in a curved or ramped surface 316 sloping to an apex 314. When the cutter 100 is properly assembled and the blade 150 is fully extended out of the blade window, as seen for example in FIG. 7B, the ramped surface 316 provides structural support and rigidity, and provides a physical stop to rotation of the blade relative to its holder 142 during cutting steps, and a physical stop to movement of the blade 150 relative to the cutter 100 during cutting steps. A pin or may pivotably connect the blade 150 to the blade holder 142 via extending through the bore 312. In another embodiment, another pivotable connection may connect the blade 150 to the blade holder 142 or directly to the blade shaft 140.

Referring to FIGS. 6A-6D, the blade 150 includes a proximal or attachment end 330, a distal end 332, and a curved blade body 334 extending therebetween along a blade length. The attachment end 330 includes first and second extensions 336, 338 which project proximally from the blade body 334, and include bores to receive a connecting pin. The body extensions 336, 338 are separated by a gap 339 shaped to receive the receiver boss 310. The curved blade body 334 may be reduced in its width relative to the first and second extensions 336, 338, as seen in FIGS. 6B and 6C.

The blade body 334 is shaped as a loop, looping from the extensions 336, 338 at a blade front side 340 on a blade first leg 341, forming a U-shaped terminal curve 342 at the distal end 332, back to the extensions 336, 338 at a blade back side 344 on a blade second leg 343. The blade 150 may also be described as lasso-shaped or banana-shaped. A curved void 346 extends from the extensions 336, 338 to the terminal curve 342, separating the blade first leg 341 from the blade second leg 343. The curved void 346 provides passage for bone fragments and other materials moved by or encountered by the blade 150 during use. A blade first side 348 extends between the first extension 336 and the distal end 332, and a blade second side 350 extends between the second extension 338 and the distal end 332, opposite the blade first side 348. Thus, the blade first side 348 includes portions of both the first and second legs 341, 343, as does the blade second side 350. The first and second legs 341, 343 may be parallel to one another, separated by the width of the void 346.

A furrow or blade relief 352 is recessed into the blade body, the blade relief 352 continuous from the blade front side 340 on first leg 341 onto the blade back side 344 on the second leg 343. Opposite the blade relief 352 is a rounded ridge 353, which is also continuous from the first leg 341 on to the second leg 343, and forms the boundary of the curved void 346. Put another way, the blade front side 340 and the blade back side 344 each include a concave curvature along their respective lengths, the concave curvature centered along the midline of the blade length to reduce the contact area at the cutting surface and thus reduce the drag forces on the blade. Opposite the concave curvature is a convex curvature. The blade first side 348 terminates laterally in a first cutting edge 356, and the blade second side 350 terminates laterally in a second cutting edge 358 which projects opposite from the first cutting edge. Thus, a curved cutting edge having an open ended U shape is formed on either side of the blade 150, enabling cutting to occur whether the cutter 100 is rotated clockwise or counterclockwise. The blade 150 is bilaterally symmetrical relative to a longitudinally extending midline, generally demarcated by the center of the blade relief 352, between the first side 348 and the second side 350. A first sloped surface 360 slopes from the first cutting edge 356 to the ridge 353, and a second sloped surface 362 slopes from the second cutting edge 358 to the ridge 353. The sloped surfaces 360, 362 may facilitate movement of severed material toward the void 346 and away from the cutting edge to prevent clogging during operation of the cutter 100. In another embodiment of the invention, the blade body may include a single cutting edge, enabling unidirectional cutting when the cutter 100 is rotated in one direction. In another embodiment of the invention, rotation of the cutter 100 may be limited to a single direction.

Viewed in cross-section as in FIG. 6D, the blade legs 341, 343 are each generally V-shaped. The cutting edges 356, 358 form the opposing lateral tips of the V, and the blade relief 352 and ridge 353 form the bottom of the V. Because the blade is looped, a cross-section of the entire blade to include both blade legs results in twin V shapes which are back-to-back, or facing away from one another, and separated by the void 346, as seen in FIG. 6D. It is also noted that each leg 341, 343 is curved in at least two planes: from the first side 348 to the second side 350, and from the proximal end 330 to the distal end 332. The shape of each leg may be described as an elongated hyperbolic paraboloid, or as an elongated saddle shape. The blade relief provided by the shape of the blade reduces friction as the blade is rotated during a cutting procedure.

In the embodiment shown, the blade 150 is a monolithic entity composed of a rigid material, in order to provide sufficient rigidity during cutting processes to cleanly cut through softer tissues such as cartilage, and harder materials such as cancellous bone, and particularly, cortical bone. The blades disclosed herein may be composed of stainless steel. The blade 150 may be provided in a variety of sizes, varying in length, width, curvature, and/or thickness. A practitioner may select the appropriate sized blade for the patient and attach the blade to the cutter 100.

The blade shaft 140, blade holder 142 and blade 150 form a blade assembly 155. The blade assembly 155 is modular and may be inserted and removed from the cutter 100 as needed, for example to change blades. The blade 150 and blade holder 142 may be provided in a variety of shapes, lengths, widths, curvatures and/or angles in order to create the desired size and shape of cavity when the cutter is deployed. By way of non-limiting example, the radius of curvature between the proximal 330 and distal 332 ends of the blade 150 vary, as may the radius of curvature between the first and second cutting edges 356, 358, in different embodiments of the blade. The length of the blade 150 from proximal 330 and distal 332 ends may vary, as may the depth between the front side 340 and the back side 344, and/or the width between the between the first side 348 and the second side 350. The blade holder 142 may be provided in a variety of lengths, and the angle of the ramped surface 314 may vary.

Figure 7A:
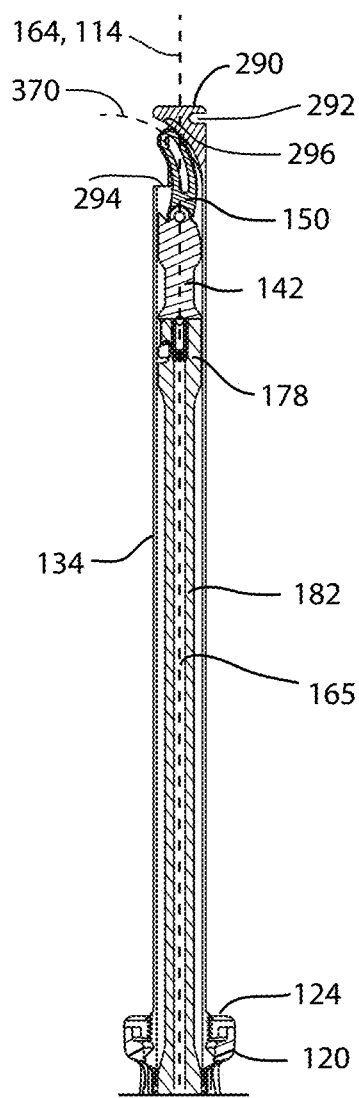
FIG. 7A is a longitudinal side cross-sectional view of a shaft portion of the cutter of FIG. 2A with the blade in the retracted configuration.
Figure 7B:
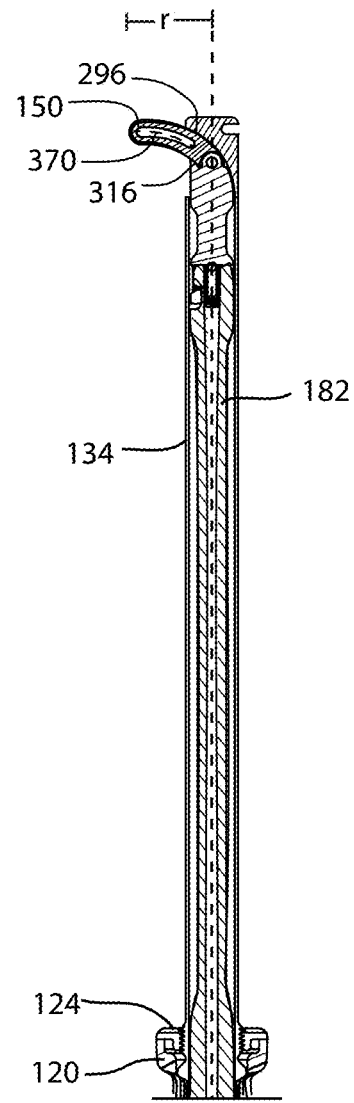
FIG. 7B is a longitudinal side cross-sectional view of the shaft portion of the cutter of FIG. 2A with the blade in the extended configuration.

FIGS. 7A and 7B are cross-sectional views of the shaft 104 and blade 106 portions of cutter 100. During assembly of the cutter, the outer tube 134 may be attached to the handle portion 102 to form a housing assembly 145. The blade 150 may be attached to the blade holder 142; in some embodiments the blade and blade holder may be provided pre-assembled. The blade holder 142 is snapped to the blade shaft 140 as described herein. The blade assembly 155 can be inserted into the housing assembly 145 in a proximal to distal approach, with the blade 150 leading through knob 122 and handle 120. The indicia on the blade shaft 140 and on the handle 120 can provide guidance as to the proper orientation of the blade shaft about its longitudinal axis 164 as the blade assembly 155 is inserted. When the blade assembly 155 is fully inserted and in the retracted or stowed configuration, the blade 150 rests inside blade window 294 at the distal end of the housing assembly 145, and the blade 150 is generally longitudinally aligned to extend along the cutter axis 114.

To employ the cutter 100 at a procedure site, the cutter distal end 290 is positioned at the site. To extend the blade 150 from the stowed configuration, torque may be applied to knob 122 to rotate it in a first direction such as clockwise, wherein the knob 122 engages the engagement feature 166 of blade shaft 140 to translate the blade assembly 155 distally along the device axis 114. As the blade assembly 155 moves distally, the blade 150 is projected laterally away from device axis 114 and out of window 294, biased by contact with ramped surface 296, which functions as a curved guide surface during blade extension. The blade distal end 332 moves along curved guide path 370 as the blade exits the window. The indicia 176 are visible through the handle window 266 and may indicate the current cutting diameter of the instrument. When a desired cutting diameter is displayed, rotation of the knob is ceased, and to perform a cutting step the entire cutter 100 may be rotated about its longitudinal axis 114 by applying torque to the handle, allowing the leading cutting edge 356 or 358 to cut through the bone or other material surrounding the exposed blade 150. The cutting step may form a circular cavity in the procedure site. After the cutting step, the knob 122 may again be actuated to further extend the blade laterally out the window 294, and the cutting step may be repeated. Extension and retraction of the blade may be ceased at any point along the curved path 370.

It is noted that during the cutting step, the blade 150 is essentially immobilized relative to the cutter 100; independent movement of the blade 250 is prevented. If the blade 150 is less than fully extended, the blade 150 is rigidly held between the bone or joint being cut and the ramped surface 296; rotational movement of the blade 150 in concert with rotational movement of the cutter 100 is permitted but movement of the blade 150, including pivotal, axial and rotational, relative to the shaft 140 and cutter 100 is prevented. When the blade 150 is fully extended, the blade 150 is rigidly held between the opposing curved surfaces 316 and 296 in a locked position; rotational movement of the blade 150 in concert with rotational movement of the cutter 100 is permitted but movement of the blade 150, including pivotal, axial and rotational, relative to the shaft 140 and cutter 100 is prevented.

When fully extended, the longitudinal curvature of blade 150 may match the curvature of guide path 370. By way of example, in the embodiment depicted in FIG. 7B, the concave curvature of the ramped surface 296 matches the convex curvature of the blade second leg 343 and blade holder 142 when the blade 150 is fully extended out of the blade window, to provide structural support and rigidity, and to provide a physical stop to independent movement of the blade 150 relative to the shaft 140 and cutter 100. The blade extension and cutting steps may be repeated as desired to create a cavity of a selected diameter at the procedure site. When cutting is completed, the knob 122 may be turned in a second direction such as counter-clockwise to translate the blade shaft 140 proximally and retract the blade 150 into the window 294, and the cutter may be withdrawn from the procedure site. Optionally, the cutter 100 may be inserted axially deeper into the procedure site and redeployed to deepen the circular cavity or create another cavity. Optionally, the cutter 100 may be rotated less than 360° to create a cavity that is less than a full circle.

The cutter 100 described herein may be used in a procedure to fuse a sacro-iliac joint. In a procedure, the cutter 100 may be deployed to create a cavity in the cartilage at the joint between the sacrum and the ilium, and/or in the hard cortical bone matter of the sacrum and/or ilium. Bone graft material may be inserted into the cavity, and a fusion device may be implanted across the joint to compress and fuse the joint.

Figure 8A:
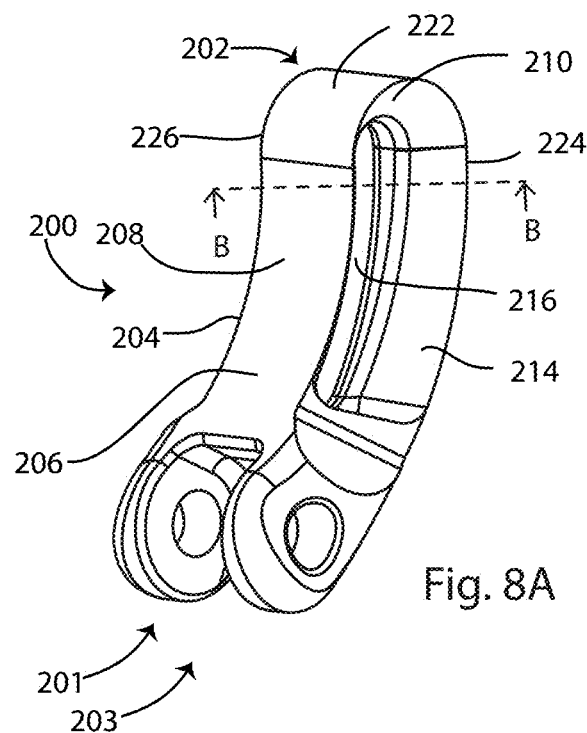
FIG. 8A is a perspective view of another embodiment of a blade for the cutter of FIG. 2A.
Figure 8B:
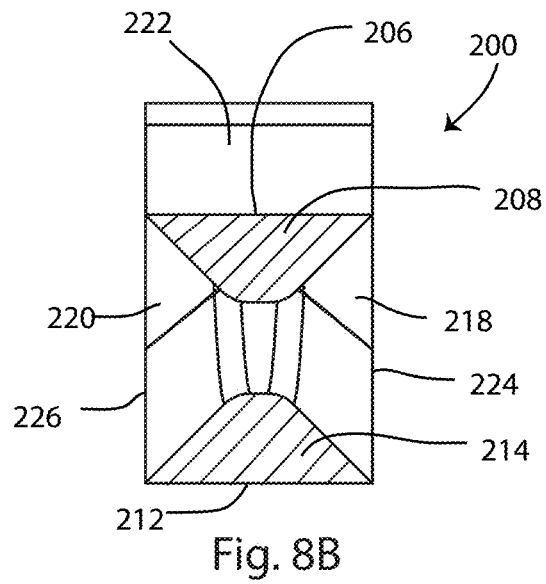
FIG. 8B is a cross-sectional view of the blade of FIG. 8A taken approximately along line B-B of FIG. 8A.

Referring to FIGS. 8A-9B, alternative embodiments of a blade for cutter 100 are shown. FIGS. 8A and 8B disclose a blade 200 having a proximal or attachment end 201, and a distal or working end 202, and a curved blade body 204 extending therebetween along a blade length. An attachment portion 203 is proximate the proximal end 201. The description of the features of the attachment end of blade 150 also applies to blades 200 and 250. The blade body 204 is shaped as a loop, looping from attachment end 201 at a blade front side 206 on a blade first leg 208, forming a U-shaped terminal curve 210 at the distal end 202, back to the attachment end 201 at a blade back side 212 on a blade second leg 214. The blade 200 may also be described as lasso-shaped or banana-shaped. A curved void 216 extends from the attachment portion 203 to the terminal curve 210, separating the blade first leg 208 from the blade second leg 214. The curved void 216 provides passage for bone fragments and other materials moved by or encountered by the blade 200 during use. A blade first side 218 extends between the attachment end 201 and the distal end 202, and a blade second side 220 extends between the attachment end 201 and the distal end 202, opposite the blade first side 218.

The blade body 204 is flat on a continuous outer surface 222 formed by the front side 206 of first leg 208, around the terminal curve 210, and the back side 212 of second leg 214. The blade first side 218 terminates laterally in a first cutting edge 224, and the blade second side 220 terminates laterally in a second cutting edge 226 which projects opposite from the first cutting edge. Thus, a curved cutting edge having an open ended U shape is formed on either side of the blade 200, enabling cutting to occur whether the cutter 100 is rotated clockwise or counter-clockwise. The blade 200 is bilaterally symmetrical relative to a longitudinally extending midline, generally demarcated by the midline center of the continuous outer surface 222, between the first side 218 and the second side 220. In cross-section as in FIG. 8B, the first leg 208 and second leg 214 are generally triangular, resulting in twin triangular shapes which are apex-to-apex, or facing away from one another, and separated by the void 216. The other features of blade 150 also apply to blade 200, including the void, and the sloped surfaces extending from the cutting edges toward the void.

Figure 9A:
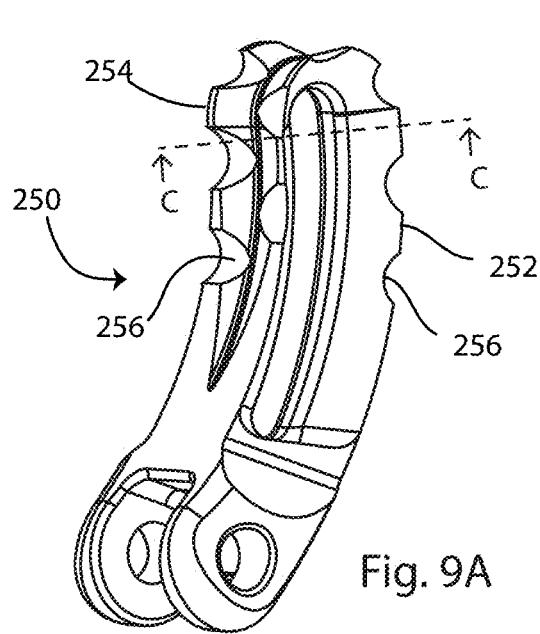
FIG. 9A is a perspective view of another embodiment of a blade for the cutter of FIG. 2A.
Figure 9B:
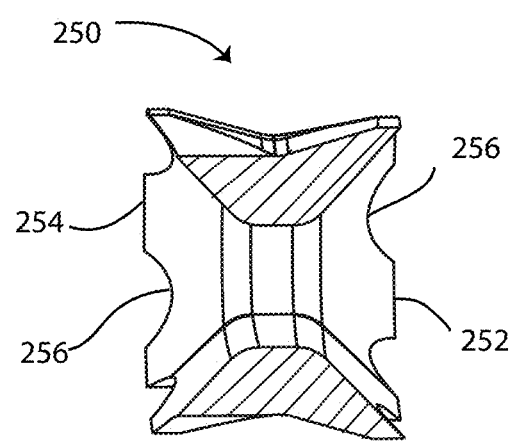
FIG. 9B is a cross-sectional view of the blade of FIG. 9A taken approximately along line C-C of FIG. 9A.

FIGS. 9A-9B disclose another alternate embodiment of a blade for use with cutter 100. The description, form and features of blade 150 apply to blade 250, with the exception of the cutting edges. Blade 250 includes first 252 and second 254 cutting edges which are broken up by scallops or serrations 256. The serrations 256 may vary in size along different portions of the blade 250, and may extend inward as far as the longitudinally extending midline of the blade. When deployed in cutter 100, the serrations 256 may facilitate cutting through hard cortical bone material.

A method of fusing a joint is set forth below. It is appreciated that although the method described is for a sacro-iliac joint, the method can be applied to any joint, or to fusion of any two bones or bone portions. In addition, the instruments and/or methods described herein may be applied to other procedures, including at least: intramedullary osteotomies for limb-lengthening, derotation, and/or malunion procedures; spinal disc space joint preparation for arthrodesis, arthroplasty and/or other procedures; and subtalar joint preparation for ankle fusion. The cutter 100 may be advantageously used to cut both soft cancellous bone and hard cortical bone.

Referring to FIGS. 10-27, systems and methods for preparing a joint space and implanting a fusion implant are shown. The method may include one or more of the following steps described below. It is understood that in certain embodiments of the method, the steps may or may not be performed in the order set forth below, one or more of the steps may be omitted, one or more of the steps may be repeated, and/or additional steps may be performed. In other embodiments of the invention, the systems and methods described herein may be used to fuse two bone portions, or two bones.

FIGS. 10-22 include a stylized cross-sectional depiction of a meeting of an ilium 6 and a sacrum 5 at a sacro-iliac joint 2. At the joint 2, the portion of the ilium depicted may include primarily hard cortical bone. The sacrum 5 is depicted as having three strata; hard cortical sacral bone 4, the sacral ala 7 and the sacral vertebral body 9. It is appreciated that the natural joint 2 between the ilium 6 and sacrum 5 undulates, as do the strata of the sacrum 5, with the natural anatomy of the bones; in the figures they are depicted as straight lines for clarity.

Figure 10:
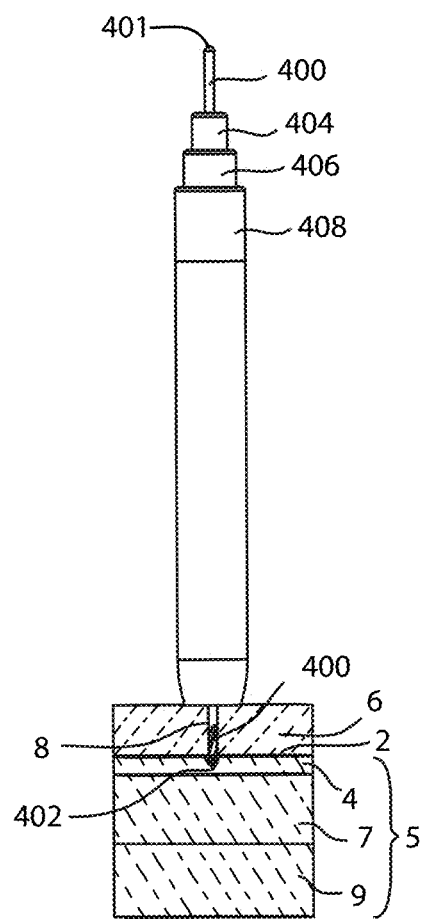
FIG. 10 is a view of a guide wire inserted to cross a joint of a first bone and a second bone at a procedure site, and a set of dilators mounted over the guide wire.

Referring to FIG. 10, in a step a guide wire is introduced into a procedure site, in the example shown a sacro-iliac joint 2 between a sacrum 5 and an ilium 6. In the embodiment shown, the guide wire is introduced through the ilium, and into the joint space, so that the tip of the guide wire is in the joint space. The guide wire may comprise a guide line, guide pin, k-wire, or another guiding line known in the art. The guide wire may create an access passageway 8 through skin, muscle and other tissues from outside the patient to the sacro-iliac joint. In one embodiment, a first guide wire comprising a 2 mm k-wire may be introduced, removed, and a larger diameter guide wire 400 is introduced through the access passageway 8 created by the first guide wire. The guide wire may be positioned so that a tip 402 of the larger diameter guide wire 400 protrudes through the ilium 6 across the joint 2 and into the bone 4 of the sacrum 5. In one embodiment, the guide wire 400 may be a 3.2 mm k-wire. Following introduction of the guide wire 400, in another step one or more cannulated dilators 404, 406, 408 may be sequentially introduced over a proximal end 401 of the guide wire 400 toward the procedure site, to further increase the diameter of the access passageway 8. In the example shown, three dilators are introduced sequentially, in ascending diameter size, over the guide wire 400. Each dilator may be inserted concentrically over the guide wire and previous dilator(s) until a distal end of the dilator, for example distal end 410 of dilator 408 contacts the ilium 6. In another embodiment of the method, one or more steps of the method may be performed without utilizing guide wires. In another embodiment of the method, a computerized navigation system may be used to guide the instrumentation and steps of the system.

Figure 11:
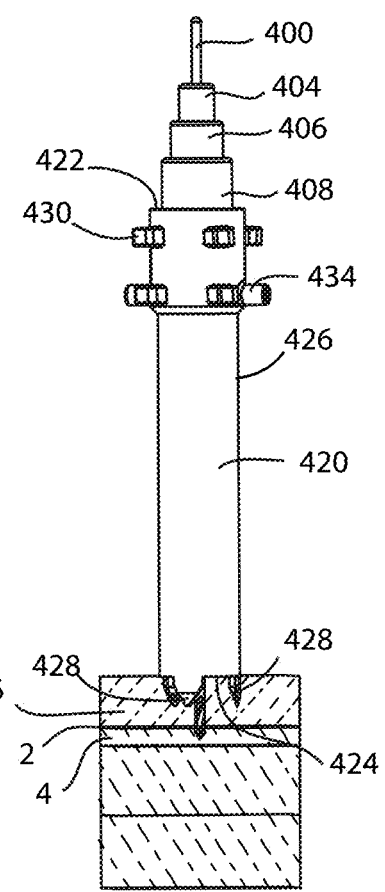
Figure 14A:
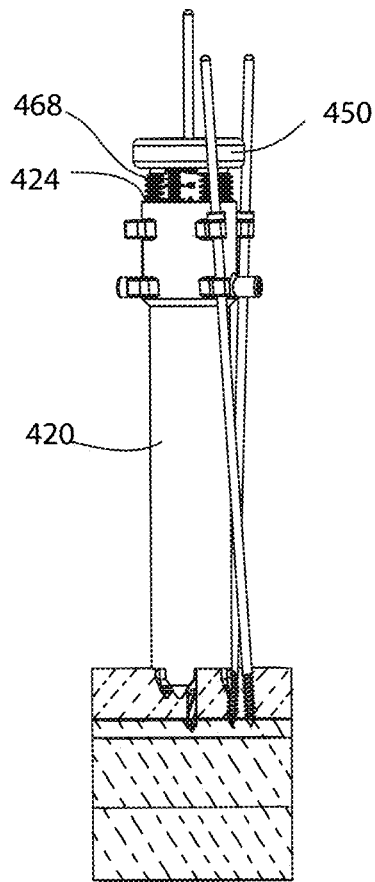
FIG. 14A is a view of the cannula of FIG. 11, with a sleeve partially received in a bore of the cannula.
Figure 24:
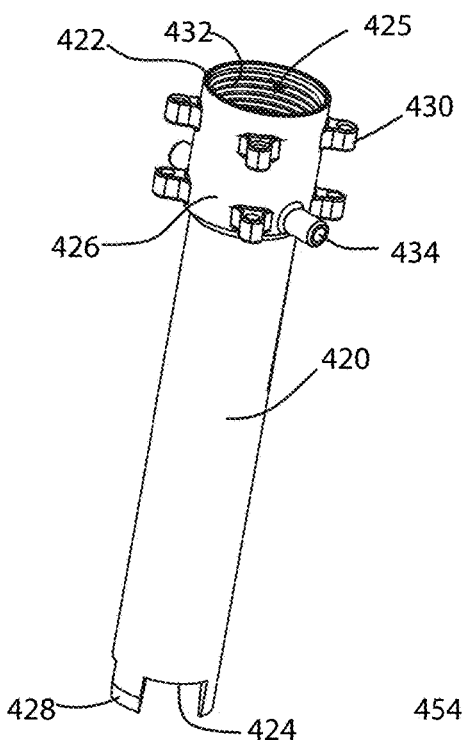
FIG. 24 is a perspective view of the cannula of FIG. 11.

Referring to FIGS. 11, 14A, and 24, in another step an access cannula 420 is introduced over the guide wire 400 and dilator(s). The access cannula 420 includes a proximal end 422 and a distal end 424, with a peripheral wall 426 extending therebetween, surrounding an internal bore 425. The cannula 420 may include one or more distally projecting teeth 428 which may protrude into the ilium 6 to dock the cannula to the ilium and stabilize the position of the cannula. The cannula 420 may further include one or more brackets 430 or other attachment features to connect to stabilizing elements such as wires or struts. The brackets 430 may be specifically shaped and/or angled to hold the stabilizing elements in a desired alignment. A portion of the peripheral wall 426 includes internal threading 432, and one or more access ports 434 may be formed in the peripheral wall 426. Upon introduction into the procedure site, the teeth 428 may protrude several millimeters into the ilium, but in the embodiment shown, preferably do not extend into the joint 2.

Figure 12:
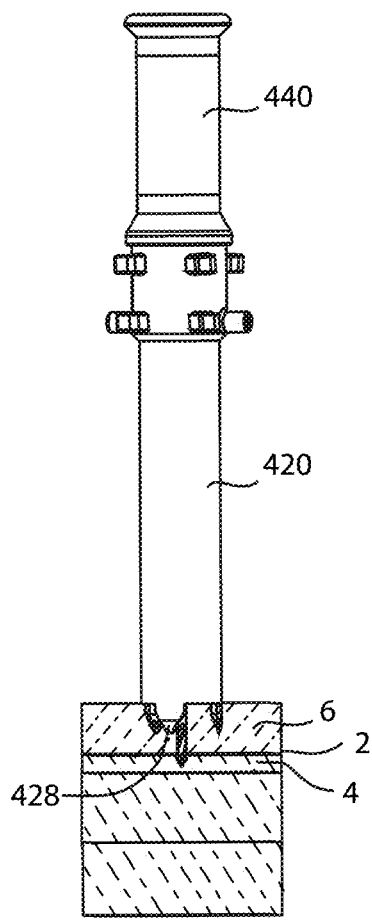

Referring to FIG. 12, in another step an impactor 440 may be connected to the proximal end 422 of the cannula 420 to drive the teeth 428 into the ilium and more securely fix the cannula in place. A mallet or other tool (not shown) may be used to apply axial force to the impactor 440.

Figure 13:
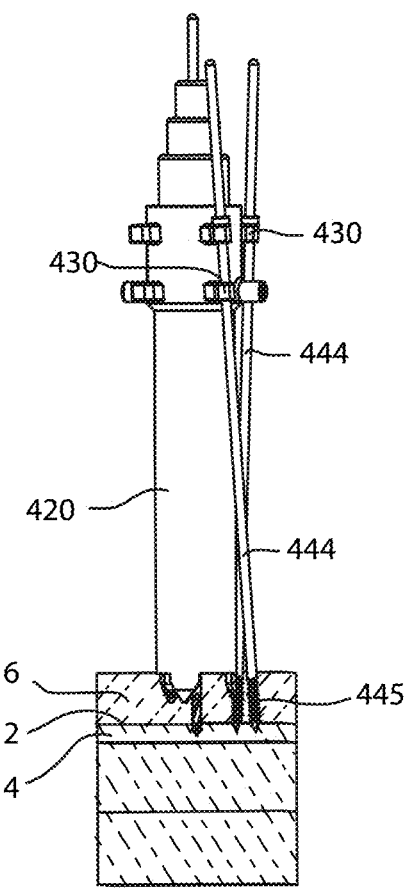

Referring to FIG. 13, following the docking of the cannula into the ilium, in another step one or more stabilizing guide wires 444 may be connected to the brackets 430 and distal ends 445 of the guide wires 444 introduced into the ilium 6, to further stabilize the position of the cannula 420 for subsequent steps of the method. When the cannula 420 is satisfactorily positioned and stabilized, the dilator(s) 404, 406, 408 may be proximally withdrawn from the cannula, over the guide wire 400.

Figure 14B:
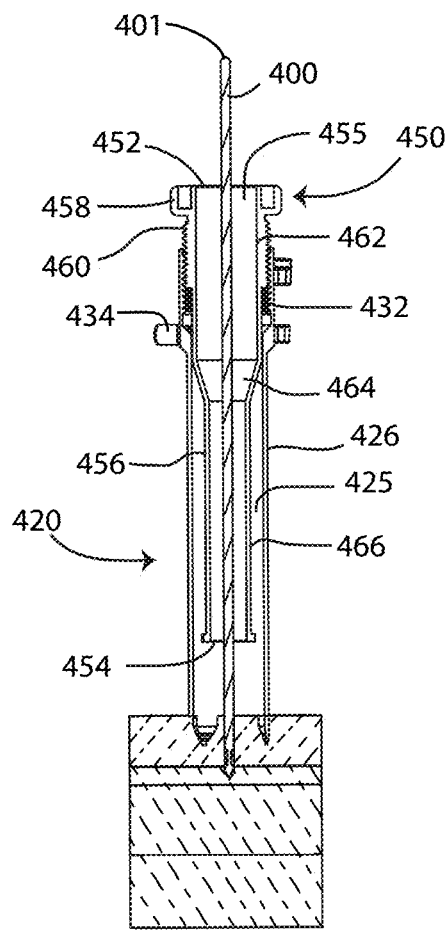
FIG. 14B is a longitudinal cross-sectional view of the cannula, guide wire and sleeve of FIG. 14A.
Figure 25:
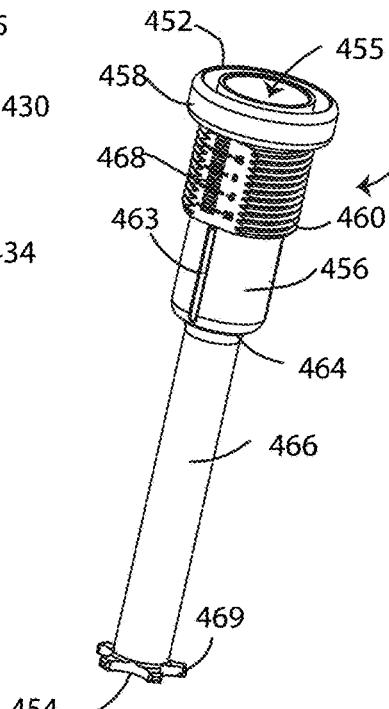
FIG. 25 is a perspective view of the sleeve of FIG. 14A.

Referring to FIGS. 14A, 14B and 25, in another step a sleeve 450 is introduced over the guide wire 400 and into the proximal end of the cannula 420. The sleeve 450 includes a proximal end 452, a distal end 454 and a sleeve body 456 surrounding a longitudinal sleeve bore 455. A rim 458 encircles the sleeve body 456, and a portion of the sleeve body includes external threading 460 for engagement with the access cannula 420, forming an adjustment mechanism with the cannula. The sleeve body 456 may include a proximal section 462, a neck 464 and a distal section 466. The diameter of the sleeve bore 455 may decrease from the proximal section 462 to the distal section 466, tapering in the neck 464. A flange 469 projects outwardly from the distal section 466 and may stabilize the distal section with respect to the access cannula 420.

The sleeve 450 may include indicia 468 so that as the sleeve 450 is engaged with the access cannula 420, a precise distance to the cannula distal end 424, and thus the procedure site, may be achieved. The combined axial length of the sleeve 450 and cannula 420 may be adjusted along a continuum by rotation of the sleeve 450. This adjustability allows precise placement of the cutter blade 150 at the joint 2, and may prevent over-insertion of the cutter 100 or other instrumentation. At least one ball detent may be received in a cannula access port 434, and interact with a groove 463 formed on the exterior of the sleeve body 450 to provide tactile indication of the extent of the sleeve rotation. The reduced inner diameter of the sleeve distal section 466 may precisely target instrumentation such as cutter 100 toward the procedure site.

Figures 15, 17:
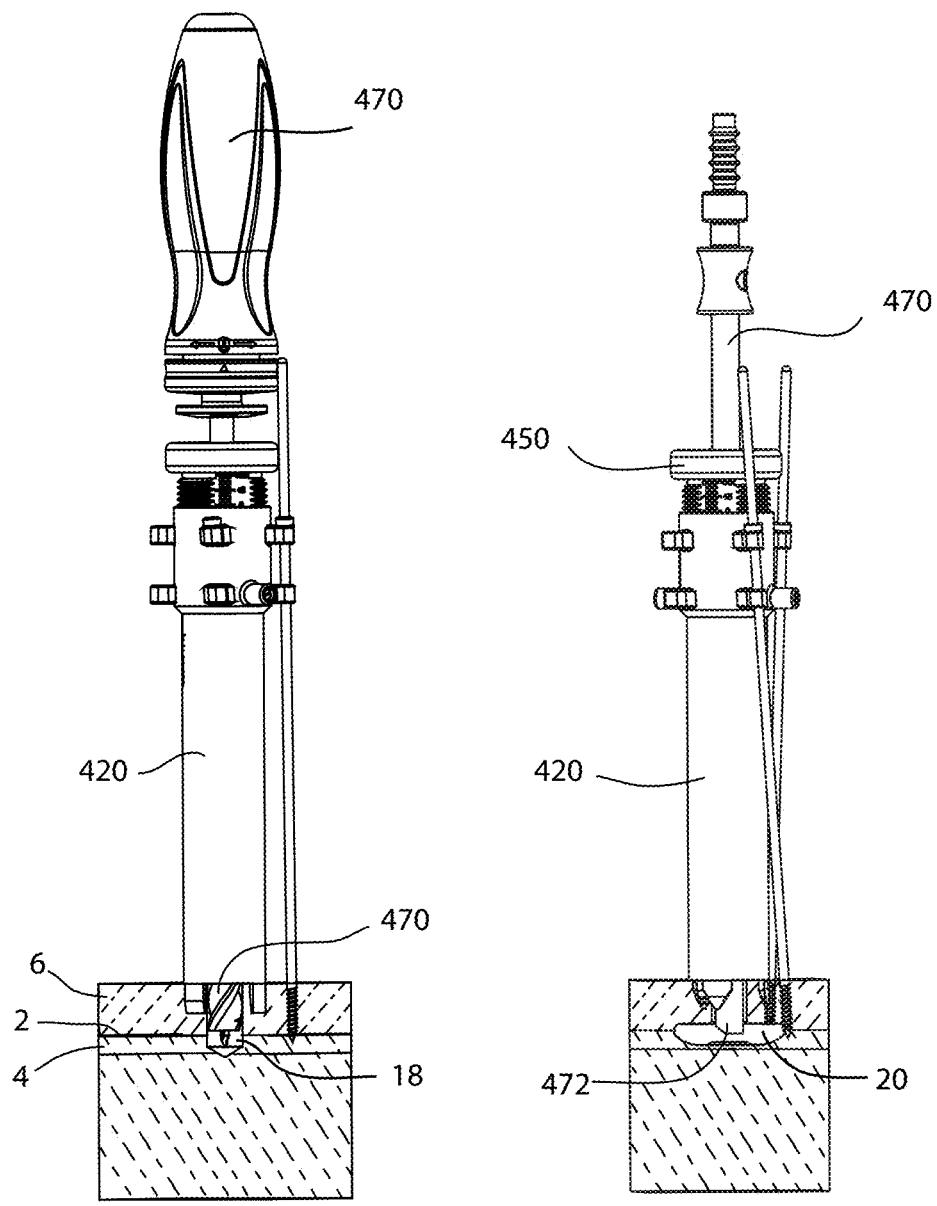

Referring to FIG. 15, in another step a drill 470 is introduced over the guide wire 400 and through the sleeve bore 455 and cannula bore 425. A first passageway 18 is drilled through the ilium 6, across the joint 2, and into the sacrum, and replaces the access passageway 8. After the drilling step, the guide wire 400 may be withdrawn from the access cannula 420. Suction may be applied to remove material from the first passageway 18.

Figures 16A, 16B:
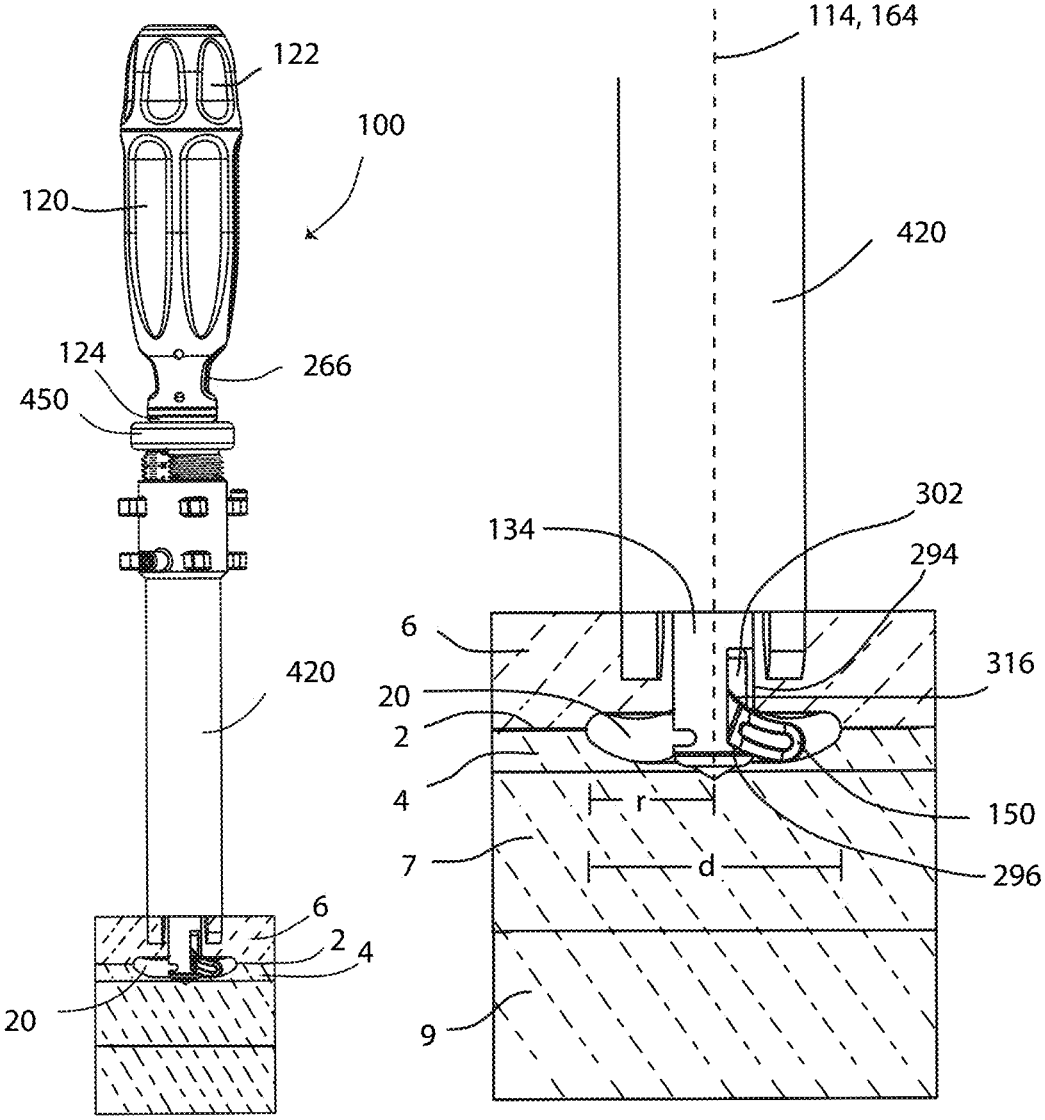
FIG. 16A is a view of the cannula and sleeve of FIG. 14A, with the cutter of FIG. 2C inserted into the cannula and sleeve, the cutter blade in the extended configuration, and a circular cavity cut into the first bone and second bone across the joint.
FIG. 16B is a close-up view of the distal end of the sleeve and cutter of FIG. 16A, also showing a cutting radius r of the cutter and a diameter d of the cavity.
Figure 16C:
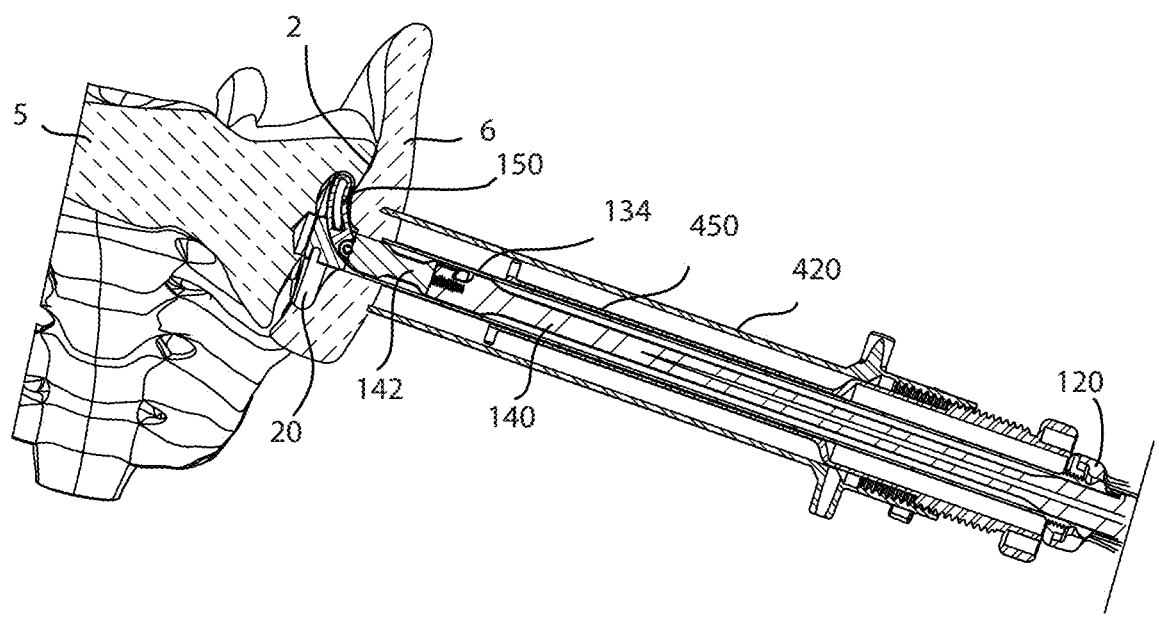
FIG. 16C is a cross-sectional view of the cutter shaft portion, cannula and sleeve of FIG. 16A cutting a cavity in a sacro-iliac joint.

Referring to FIGS. 16A and 16B, in another step the cutter 100 is introduced, with the shaft portion 104 inserted through the sleeve 450, cannula 420, and first passageway 18. The cutter distal end 112 may contact the sacrum 5, and the blade 150 within blade window 294 are positioned past, or distal to, the distal end 424 of the cannula 420. During the introduction step, the blade 150 is in the retracted configuration, so that it is contained within a diameter envelope of the outer tube 134. The handle distal end 124 may contact the rim 458 of the sleeve, limiting the insertion depth of the cutter 100. The sleeve 450 may be rotated as needed to adjust the depth of the cutter distal end 112. Fluoroscopy may be utilized as desired to visualize notch 292 and blade window 294, allowing precise placement of cutter 100 relative to the joint 2 at the procedure site.

When the cutter shaft 104 and blade 106 portions are at the desired location, and the blade portion 106 is distal to the cannula distal end 424, in one or more steps knob 122 is rotated to deploy the cutter blade 150 laterally. During initial deployment, only a small portion of the blade 150 may project laterally out of the blade window, the blade distal end 332 extending to a first deployed distance r, measured as the distance from the cutter longitudinal axis 114 to the blade distal end 332, perpendicular to the axis 114. The deployed distance represents the radius of a circle which may be cut by the cutter blade. The practitioner may check the deployed distance by reading the indicia 176 visible in the indicator window 266. In embodiments of the device, the indicia 176 indicate the diameter of a circular cavity cut by the device. In embodiments of the device, the diameter cut by the cutting device 100 may range from 2 mm to 70 mm, and the cutting radius or deployed distance r may range from 1 mm to 35 mm. Blades 150 of varying lengths may be provided to attain the range of cutting diameters disclosed herein.

In another step, torque is applied to the handle 120 to rotate the entire cutter 100 about its longitudinal axis, thus sweeping the blade 150 in a circular path to perform a first cut. The cutting edge 356 or 358 at the leading side of the blade 150 cuts into the surrounding bone and/or other tissue. Fragments of the bone and/or tissues are severed from the joint and are urged toward the void 346, the leading sloped surface 360 or 362 facilitating movement of the tissue fragments away from the cutting edge and toward the void 346. The blade 150 cuts a cavity having a diameter determined by the distance between the cutter longitudinal axis and the blade distal end 332 at its deployed distance, or r. After the first cut, the knob 122 may again be rotated relative to the handle 120 to further extend the blade laterally to a second deployed distance. The entire cutter 100 may be rotated again to perform a second cut of a larger diameter, thus increasing the diameter of the cavity. These steps may be repeated as needed until the desired diameter cavity 20 is created. FIG. 7B illustrates the blade 150 at a fully deployed or fully extended configuration. At the fully extended configuration, the blade 150 is held essentially immobile relative to the cutter 100 by contact with the opposing curved surfaces 296 and 316, which act as stops to lock the blade in its extended position. At less than the fully extended configuration, the extended blade 150 is held rigid by contact with the ramped surface 296 and contact with the bone or other tissue against which the blade is deployed.

Referring to FIG. 17, in one or more steps suction may be deployed in between cutting steps, or at other points during the procedures described herein, as needed to clear debris from the cavity and/or instrument. To deploy suction, the cutter 100 or other instrument may be withdrawn from the cannula 420. A suction tool 470 may be inserted, until an opening 472 of the suction tool 470 is at a desired location in the cannula 420 or cavity 20, or pathway 18. The suction tool 470 may be connected to a suction source, and suction is applied until the debris is removed. Fluid may be applied during the suction process. In other embodiments, means for suction may be integrated into cutter 100, eliminating the need for a separate suction tool.

Figure 18:
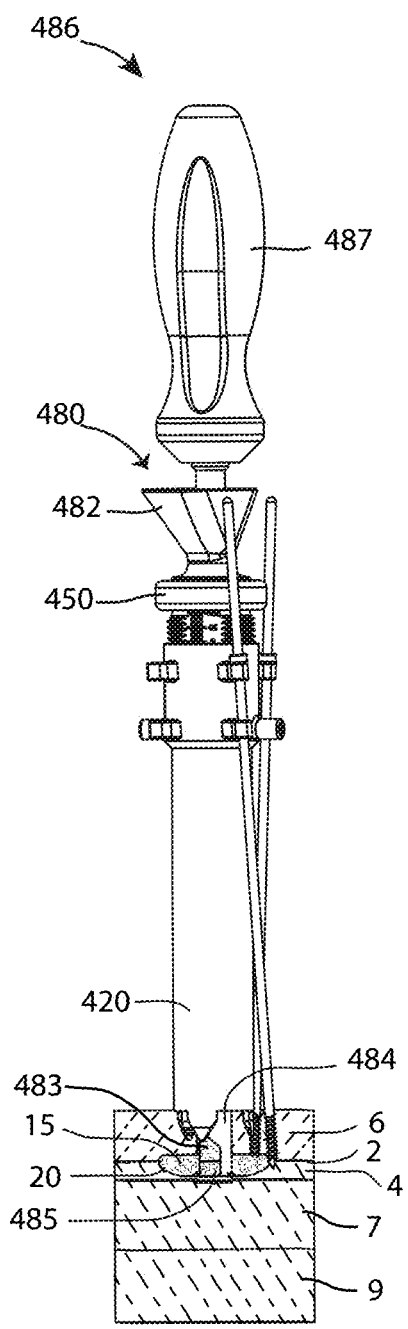
Figure 27:
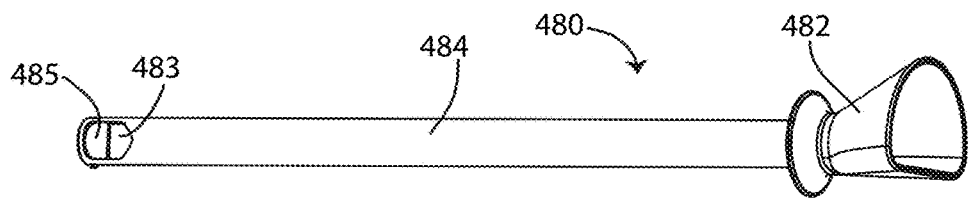
FIG. 27 is a perspective view of the graft funnel of FIG. 18.
Figure 28:
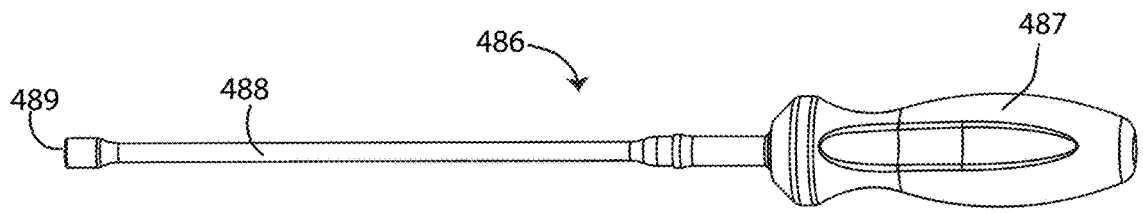
FIG. 28 is a perspective view of the tamp of FIG. 18.
Figure 29:
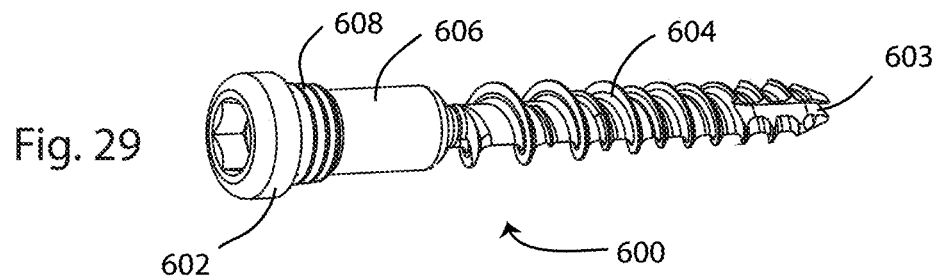
FIG. 29 is a perspective view of an alternate embodiment of a fusion device screw-type fastener.
Figure 30:
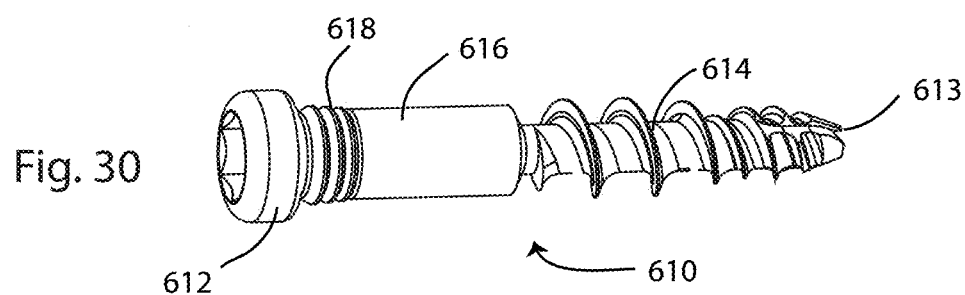
FIG. 30 is a perspective view of another alternate embodiment of a fusion device screw-type fastener.
Figure 31:
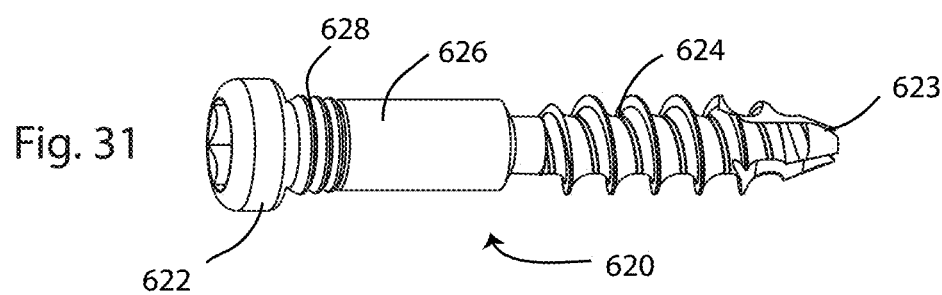
FIG. 31 is a perspective view of another alternate embodiment of a fusion device screw-type fastener.
Figure 32:
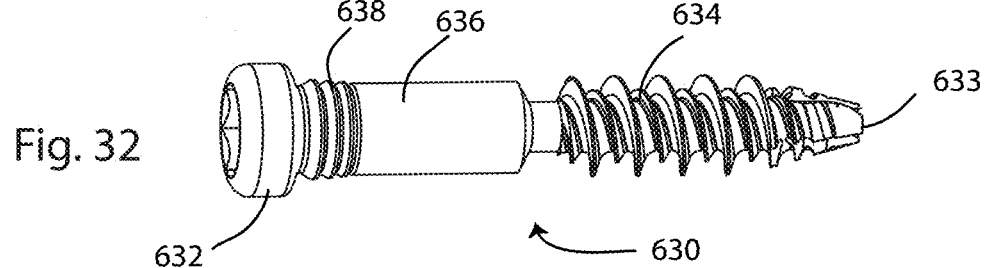
FIG. 32 is a perspective view of another alternate embodiment of a fusion device screw-type fastener.
Figure 33:
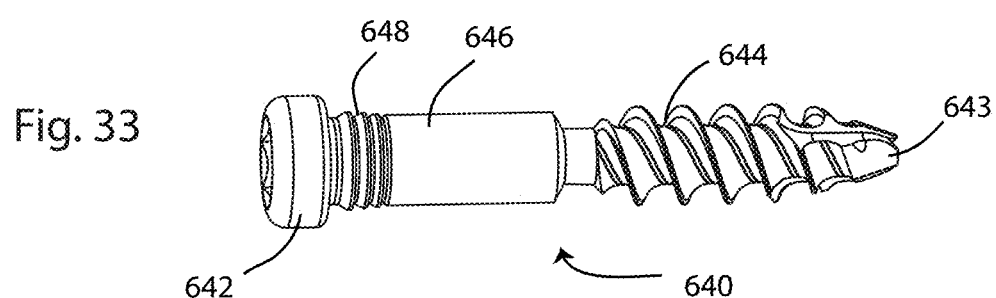
FIG. 33 is a perspective view of another alternate embodiment of a fusion device screw-type fastener.
Figure 34:
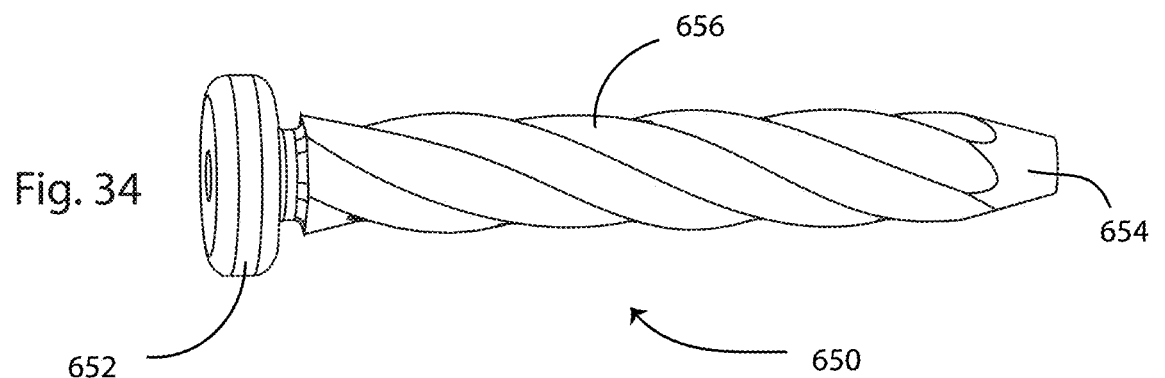
FIG. 34 is a perspective view of another alternate embodiment of a fusion device nail-type fastener.
Figure 35:
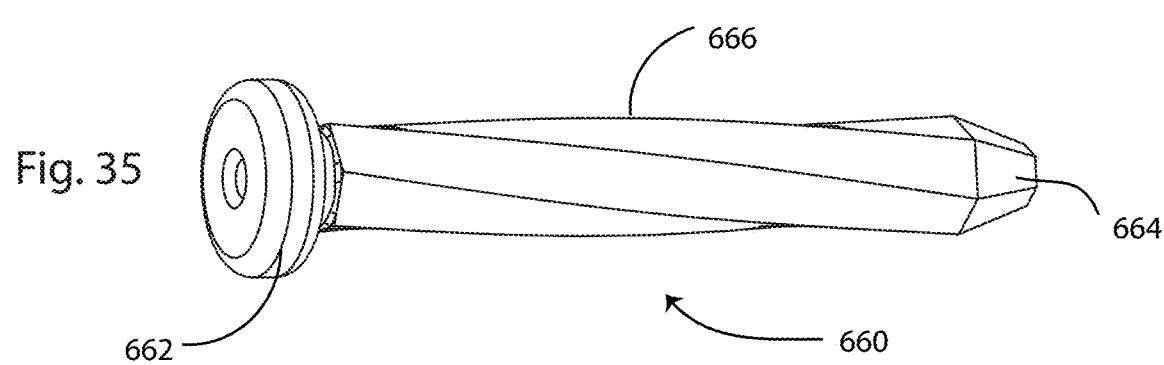
FIG. 35 is a perspective view of another alternate embodiment of a fusion device nail-type fastener.
Figure 36:
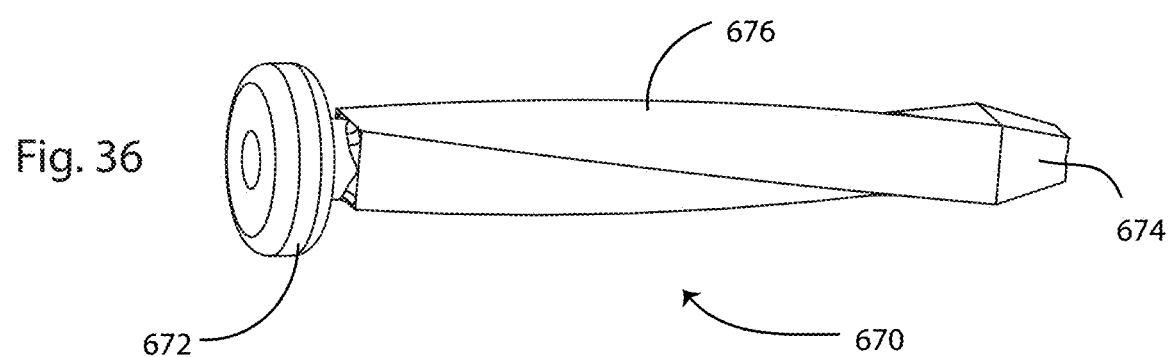
FIG. 36 is a perspective view of another alternate embodiment of a fusion device nail-type fastener.
Figure 37:
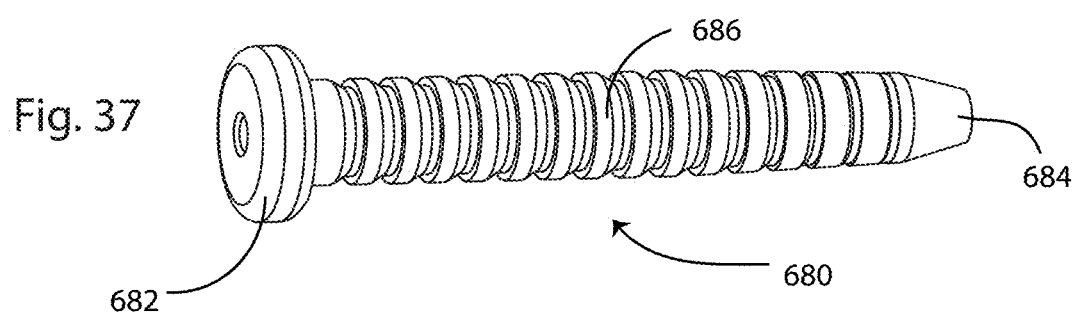
FIG. 37 is a perspective view of another alternate embodiment of a fusion device nail-type fastener.

After the cavity 20 of a desired or selected diameter is created, bone graft material and/or other substances may be introduced into the cavity. With reference to FIGS. 18 and 27, a graft funnel 480 may be used to guide bone graft material into the cavity 20. The graft funnel includes a funnel portion 482 and a conduit 484. A pair of openings 483 on opposite sides at the distal end of the conduit 484 allow movement of the graft material out of the conduit. A plug 485 in the distal end of the conduit includes guide surfaces that divert the graft material out of the opposing openings 483. In a graft insertion step, the graft funnel may be inserted to extend through the sleeve 450 and cannula 420 with the distal end of the conduit 484 opening into the cavity 20. Graft material 15 is inserted into the funnel portion 482. A tamp 486 may be used to push the graft material distally through the conduit 484 toward the plug 485, out the side openings 483 and into the cavity 20. The tamp may include a handle 487, a shaft 488 and a distal tamp face 489. In another embodiment, a tamping member with a solid distal tamp face may be coupled to the blade holder 142 of the cutter 100 and deployed by rotation of the knob 122 to push the graft material through the conduit 484 and into the cavity 20. During a graft insertion step, the funnel 480 may be selectively rotated to ensure that graft material exits the openings 483 into all or selected parts of the cavity 20.

Figure 19:
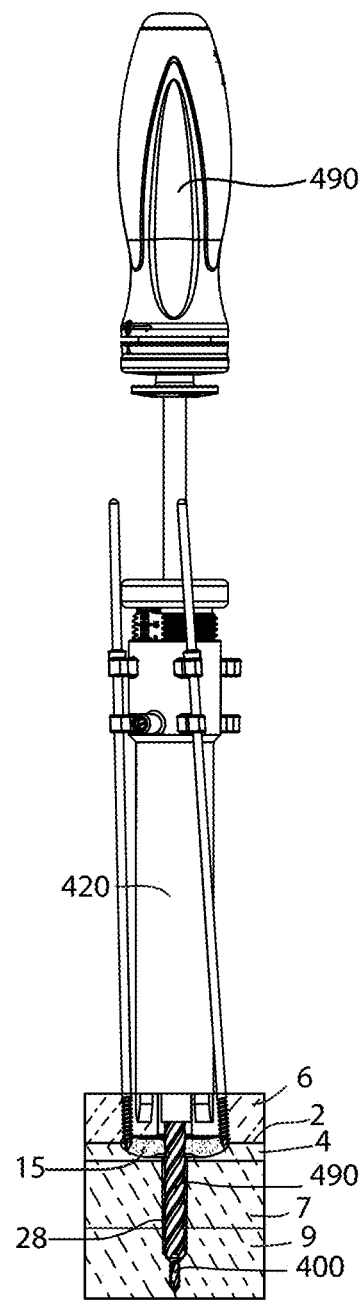

Referring to FIG. 19, in another step of the method a tunnel may be drilled through the packed bone graft and across the cavity to prepare for insertion of a fusion device. Prior to drilling the hole, a dilator such as dilator 404 may be reintroduced into through sleeve 450 into cannula 420, to provide a guide for a guide wire. The guide wire 400 may also be reintroduced, and inserted through the ilium 6, the cavity 20 and graft 15, and into the sacrum 5, extending through the hard cortical layer 4, the sacral ala 7 and into the sacral vertebral body 9. A drill 490 is introduced over the guide wire 400 to drill a second passageway 28 also extending through the bone graft and cavity and into the sacrum 5, to provide a passage for the fusion screw implant. In another embodiment of the method, both passageways 18 and 28 may be drilled prior to cutting the graft cavity 20 with the cutter 100.

Figure 20:
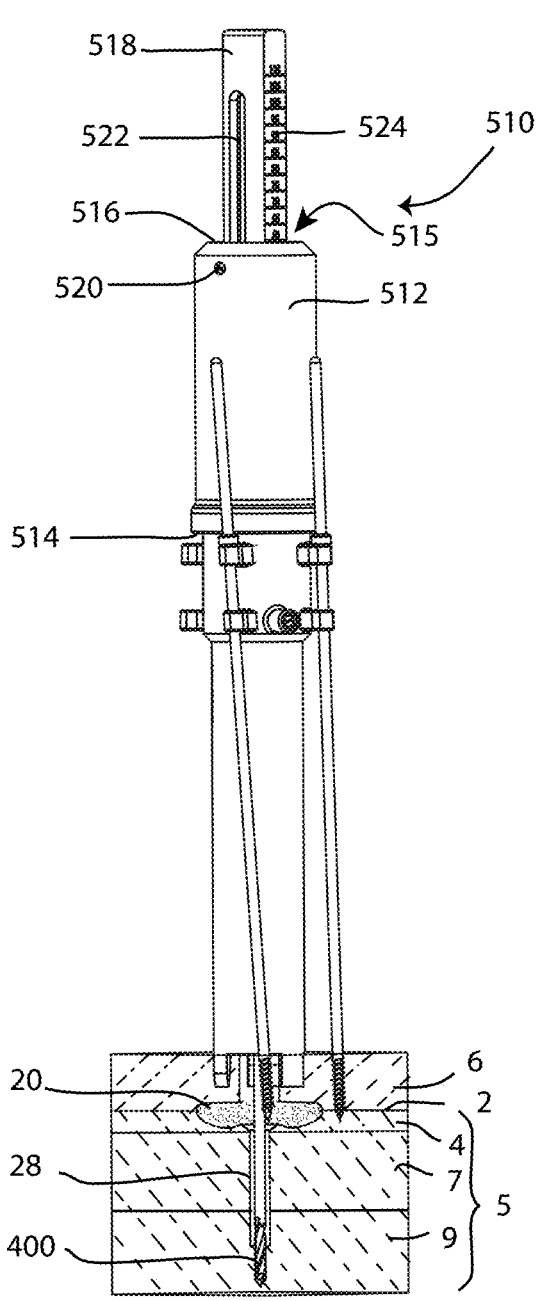
Figure 26:
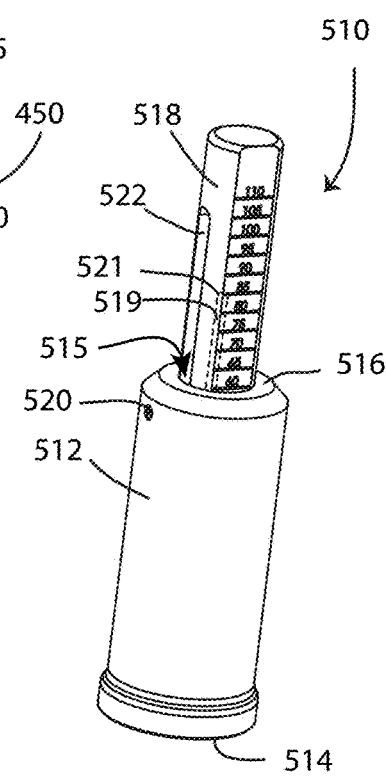
FIG. 26 is a perspective view of the length gauge of FIG. 20.

As shown in FIGS. 20 and 26, in another step of the method a length gauge 510 can be used to determine the proper length for a fusion implant. Length gauge 510 includes a support member 512 having a distal end 514, a proximal end 516, and a bore 515; and further includes a gauge 518 and set screw 520. Set screw 520 may include a ball detent. The gauge 518 is partially cannulated, having a blind bore 519 shaped to receive the proximal end 401 of guide wire 400, the blind bore having an end surface 521. The gauge 518 also includes a blind groove 22. When assembled for use, the gauge 518 is received in bore 515 of the support member 512. Set screw 520 extends through an opening in the support member 512 and into the groove 522. To measure for proper implant length, the screw length gauge 510 is mounted on to cannula 420, with the distal end 514 of the support member 512 resting on the proximal end 422 of the cannula. The guide wire 400 proximal end 401 is received in the blind bore 519 of the gauge 518. The gauge 518 may be adjusted until the end surface 521 of the blind bore 519 rests on the proximal end 401 of the guide wire 400. The proper implant length may then be indicated by indicia 524 on the gauge 518, read where the gauge 518 intersects the support member proximal end 516.

As shown in FIGS. 1, and 21-23D, in another step of the method a properly sized fusion implant 550 may be implanted into the prepared cavity 20, crossing the cavity and joint 2 and engaging the sacrum 5 and ilium 6. The fusion implant 550 includes a screw member 552 and a washer member 554. The screw member 552 includes a head 566 and a distal tip 568 with a screw body 564 extending therebetween, extending along a screw longitudinal axis 557. The head 566 is preferably spherical and has a spherical center point 569. Engagement features 567, for example a hex feature as seen in FIGS. 23B and 23C, are present in the head 556 for connection with insertion and/or removal instrumentation. The screw member 552 may include a bore or lumen 551 extending along its lengthwise dimension to allow for introduction over the guide wire 400, and may include one or more fenestrations, or apertures 556 which open into lumen 551 for graft packing and bone throughgrowth. The lumen 551 may be concentric about the axis 557. A self-tapping threaded engagement zone 558 is distal to a non-threaded lag zone 560. An annular lip 559 projecting from the screw body 564 may provide resistance to unintentional screw withdrawal, and may provide additional compression when the implant 550 is inserted across a joint. An undercut, or annular groove 561 may encircle the screw member 552 at the junction of the screw head 566 and screw body 564. The screw member 552 is smaller in diameter at the annular groove 561 than at the lag zone 560 or at the screw head 566. A distal annular surface 563 encircles the screw body 564 between the lip 559 and the annular groove 561, and is sloped relative to a transverse plane of the screw member.

As shown in FIGS. 22 and 23A-D, the lag zone 560 may be non-threaded and cylindrical. The lack of exterior threading on the lag zone 560 permits compression of the joint 2 between the engagement zone 558, and the screw head 566 and/or washer 554 as the implant 550 is implanted across the joint 2 and into the sacrum 5. In an embodiment, the diameter of the lag zone 560 is 10 mm; in another embodiment, the diameter of the lag zone 560 is 12 mm. In other embodiments of the disclosure, the diameter of the lag zone can range between about 6 mm and about 14 mm. In the context of the diameter of the lag zone, "about" is defined as +/−1 mm. In an embodiment, the outer diameter of the washer is about 24 mm, and therefore a maximum outer diameter of the implant is about 24 mm. In the context of the outer diameter of the washer, "about" is defined as +/−8 mm. In an embodiment, the maximum outer diameter of the implant is less than the diameter of the prepared cavity 20. In another embodiment, the maximum outer diameter of the implant is greater than the diameter of the prepared cavity 20.

The screw member 552 may include internal threads 562 or other features for engagement with implantation and/or removal instrumentation. Upon implantation, the engagement zone 558 may be at least partially embedded in the sacrum 5, extending into the body of the sacral vertebra 9; and the lag zone 560 may cross the ilium 6, joint 2, cavity 20, and can extend into the sacrum 5. The washer 554 abuts the ilium 6. The screw member 552 may be sized so that the lag zone 560 is positioned to extend through the ilium, and the engagement zone 558 extends into the body of the sacral vertebra 9 upon implantation, permitting engagement in the region with improved bone quality including higher bone density.

The washer 554 includes an upper or proximal side 570, a lower or distal side 572, and a semispherical capsule 553 positioned between the upper and lower sides. The semispherical capsule 553 has a spherical center point 571 and may be concavely curved, and circumscribes a bore 555 defining a central bore axis 582. When properly assembled with the screw member 552, the semispherical capsule 553 may retain the head 566 of the screw member 552, and the screw body 554 protrudes distally from the bore 555. The head 566 may be recessed below the upper side 570 of the washer. An inner diameter of the washer 554 at the lower side 572 may be approximately equal to the outer diameter of the screw member at the lip 559. In the context of the inner diameter of the washer 554 at the lower side 572 and the outer diameter of the screw member at the lip 559, "approximately" is defined as the inner diameter of the washer 554 at the lower side 572 being equal to, or up to 5% smaller than, the outer diameter of the screw member at the lip 559. Thus when the screw head 566 is properly assembled within the washer member 554 as in FIG. 23, the washer member is captive to the screw member, the projecting lip 559 preventing unintentional disassembly of the washer member from the screw member 552.

The implant 550 further includes a fusion zone 565, which is defined as extending from the distal side 572 of the washer to the proximal end of the screw member engagement zone 558, as shown in FIG. 23. The fusion zone 565 is non-threaded, and is a zone of compression and long-term fixation of the joint, between the washer and the threaded engagement zone.

A study which documented the anatomical dimensions of the sacro-iliac joint of 50 subjects was used to determine the overall length of embodiments of the implant 550, the length of the fusion zone 565, and the diameter of the screw member engagement zone 558. Computerized tomography (CT) scans of the subjects were measured, providing dimensions of the iliac width, the sacro-iliac joint space width, the sacral alar width, and the width of the body of the sacral vertebra along an ideal sacro-iliac implant trajectory 690, as shown in an axial pelvis CT in FIGS. 38A and 38B. The sacral ala is generally known to have lower bone mineral density (BMD), while the body of the sacral vertebra is known to have higher BMD. Some studies have shown a 2X increase in BMD in the body of the sacral vertebra when compared to the sacral ala. In addition, the length of a "safe zone" 688 at the boundary between the sacral ala and sacral vertebral body, and perpendicular to the trajectory 690, was measured. The safe zone length extends between the boundaries (normal to the SI joint) of an area through which a sacral fixation implant may be inserted without impinging on neural structures or soft tissues. The safe zone dimension may be used to determine the diameter of the screw member engagement zone 558. The ideal implant trajectory 690 passes normal to the SI joint and crosses the safe zone 688 at the midpoint of the safe zone, and ultimately anchors in the denser sacral vertebral body 9. Such a trajectory normal to the SI joint will provide the maximum compression during fusion, and passing through the middle of the safe zone allows the least risk to the patient.

Figure 38A:
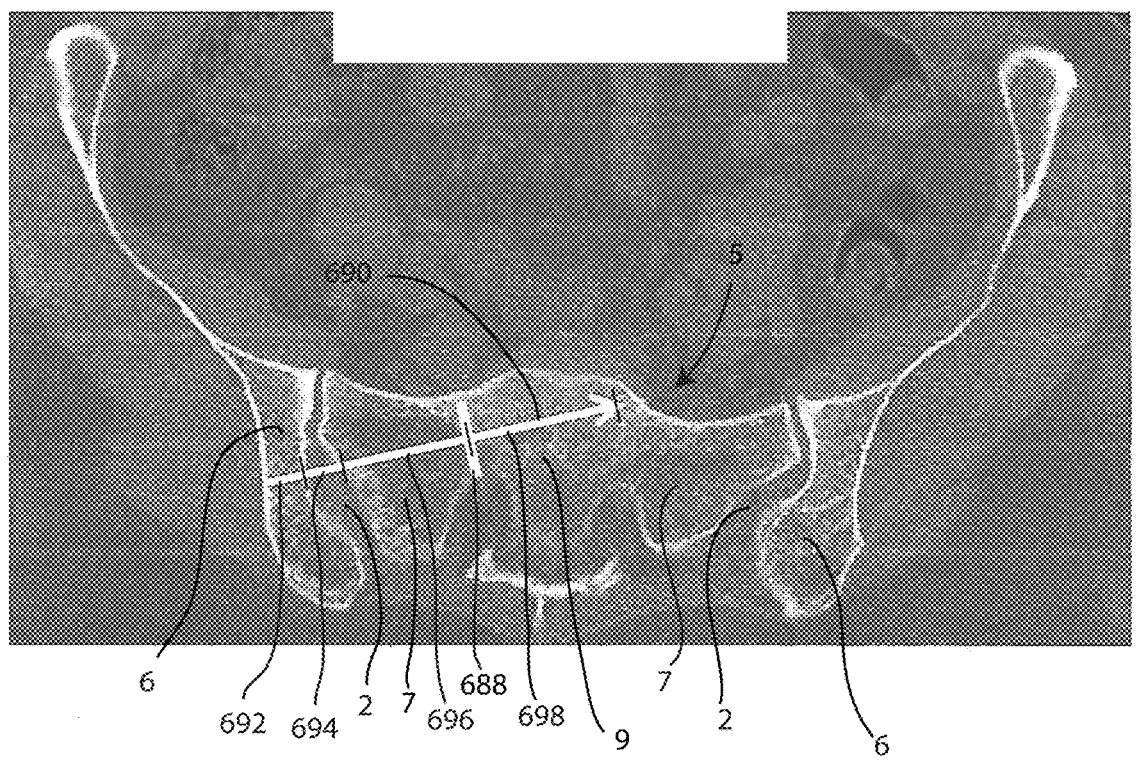
FIG. 38A is a view of an axial computer tomographic (CT) scan of a pelvis, showing an idealized trajectory for a sacro-iliac joint implant, and measurement segments along the trajectory.
Figure 38B:
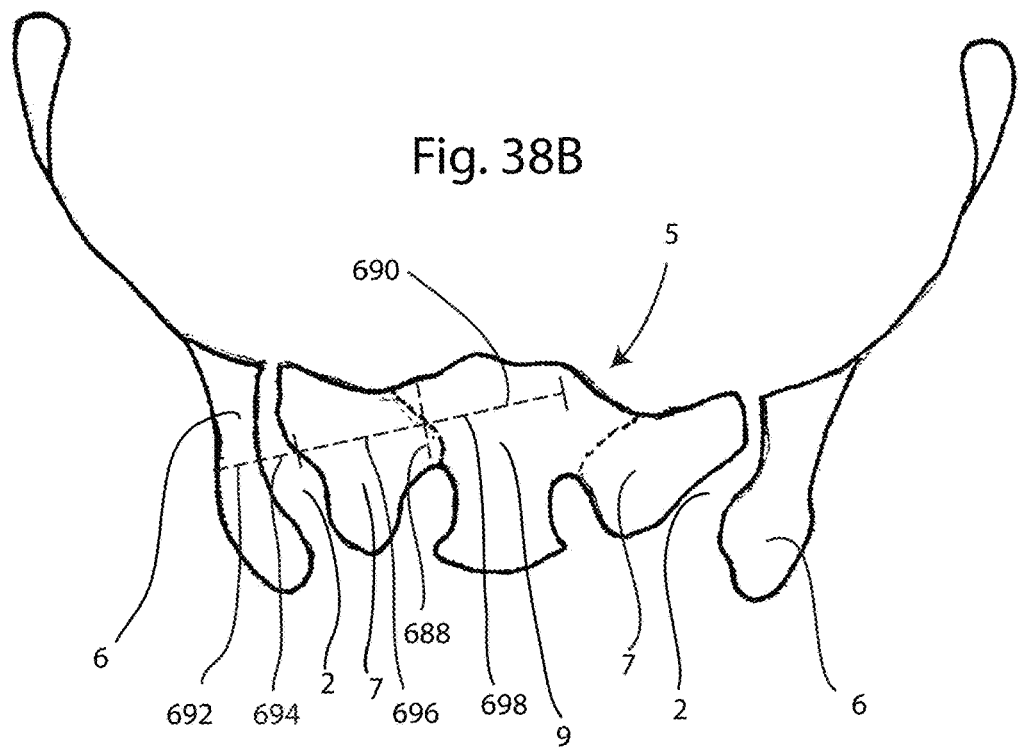
FIG. 38B is a black and white line tracing of the bony anatomy of the CT scan of FIG. 38A, showing the idealized trajectory for a sacro-iliac joint implant, and the measurement segments along the trajectory.

Referring to FIGS. 38A and 38B, segment 692 is the iliac width, segment 694 is the sacro-iliac joint space width, segment 696 is the sacral alar width, segment 698 is the sacral vertebral body width, and 688 is the safe zone length. Summary results of the study are presented in Table 1 below.

TABLE 1

Average measurements along Sacro-Iliac Implant Trajectory, in mm

|  | Iliac Width | Joint Width | Alar Width | Body Width | Safe Zone Length |
|---|---|---|---|---|---|
| Average | 15.19 | 5.75 | 31.15 | 37.24 | 17.9 |
| Max | 22.9 | 14.5 | 42.9 | 46.2 | 22.2 |
| Min | 9.6 | 2.1 | 20.7 | 25 | 13.9 |
| St. Dev. |  |  |  |  | 2.1 |

The average depth of the joint from the ilial outer surface (ilial width plus joint width) is 21 mm. Based on these study results, the length of the fusion zone 565, measured with the washer in a neutral, coaxially aligned position relative to the screw member, was designed to be 23 mm for all screw members greater than or equal to 60 mm long, and 19 mm for all screw members less than 60 mm long, in order to provide optimal fit, engagement with high quality bone, and fusion, in the sacro-iliac joint. The shorter fusion zone on shorter screw members facilitates having sufficient remaining threaded length in the engagement zone for bone purchase. However, in other examples the length of the fusion zone 565 may be directly proportional to the screw length according to this formula: FZ=mL+B, where FZ=fusion zone length, m=slope, L=screw length, and B=intercept.

The overall length of the screw member 552 may range between about 40 mm and about 110 mm. In the context of the overall length of the screw member 552, "about" is defined as +/−2 mm. Screw members 552 may be available in 5 mm increments between 40 mm and 110 mm lengths, although a screw member of any intermediate length may also be provided. The length of the fusion zone 565 may range from about 10 mm to about 37 mm long. In the context of the length of the fusion zone 565, "about" is defined as +/−2 mm. For screw members 552 greater than or equal to 60 mm long, the fusion zone 565 may be 23 mm long. For screw members 552 less than 60 mm long, the fusion zone 565 may be 19 mm long.

In an embodiment, the diameter of the screw member engagement zone 558 is 12 mm. This diameter is based on the safe zone measurements in Table 1; a 12 mm diameter allows 2 mm on either side of the screw member engagement zone 558, while remaining within the safe zone average measurement of 17.9 mm.

The semispherical connection between the head 566 and the washer member 554 permits polyaxial orientation of the screw member 552 relative to the washer member 554. The reduced diameter of the screw member at the annular groove 561 with respect to the screw body 564 enables a greater range of motion for the washer member than if the screw member diameter were not reduced. In addition, the angled distal annular surface 563 of the screw body 564 enables a greater range of motion for the washer member than if the distal annular surface were flat, or perpendicular to the longitudinal axis 557. The washer/screw connection provides at least +/−8 degrees of angulation of the washer member relative to the screw member, as defined by the position of the central bore axis 582 of the washer bore 555 relative to the longitudinal axis 557 of the screw member. The range of motion of the central bore axis 582 relative to the longitudinal axis 557 of the screw member is conical in shape, with the apex of the cone at the spherical center point 569 of the screw head 566. When the screw head 566 is properly assembled within the washer capsule 553, the spherical center point 569 is coincident with the spherical center point 571 of the washer capsule 553.

Figure 23A:
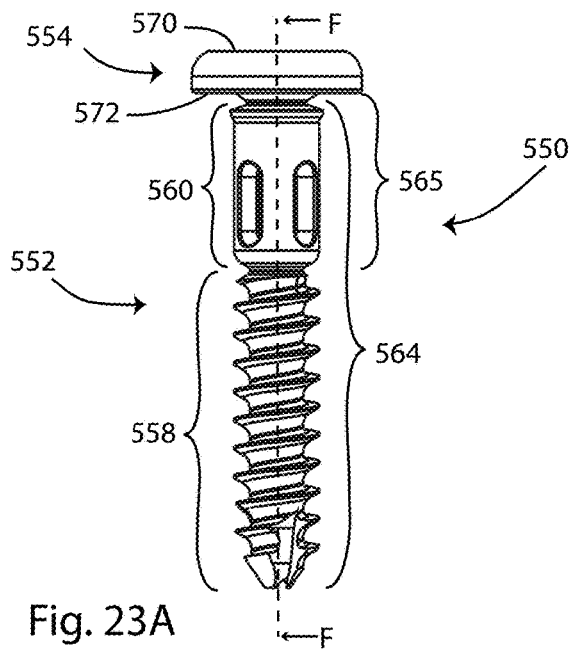
FIG. 23A is a side view of the fusion device of FIG. 1.
Figure 23B:
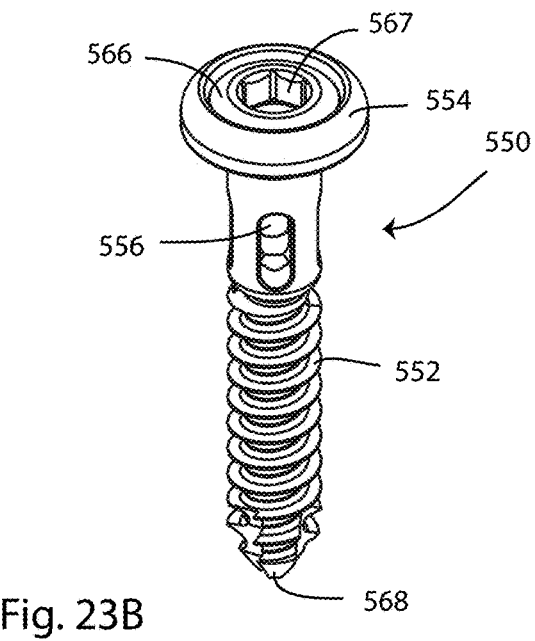
FIG. 23B is a perspective view of the fusion device of FIG. 1.
Figure 23C:
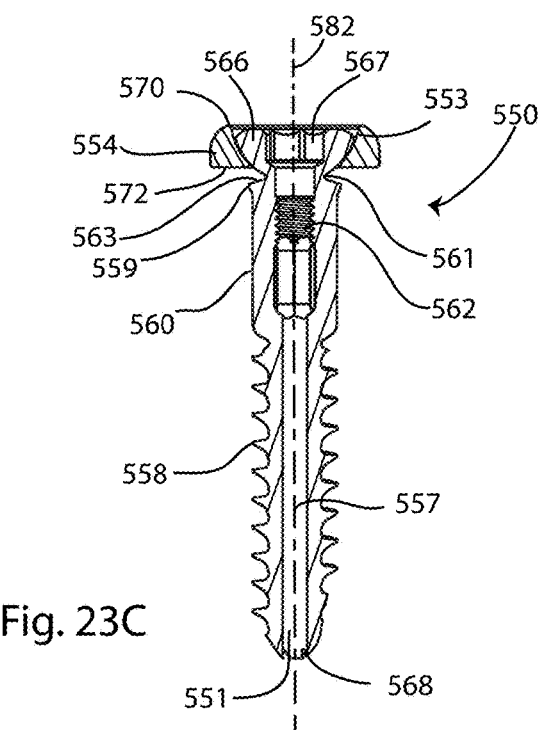
FIG. 23C is a cross-sectional view of the fusion device of FIG. 1, taken along line F-F in FIG. 23A.
Figure 23D:
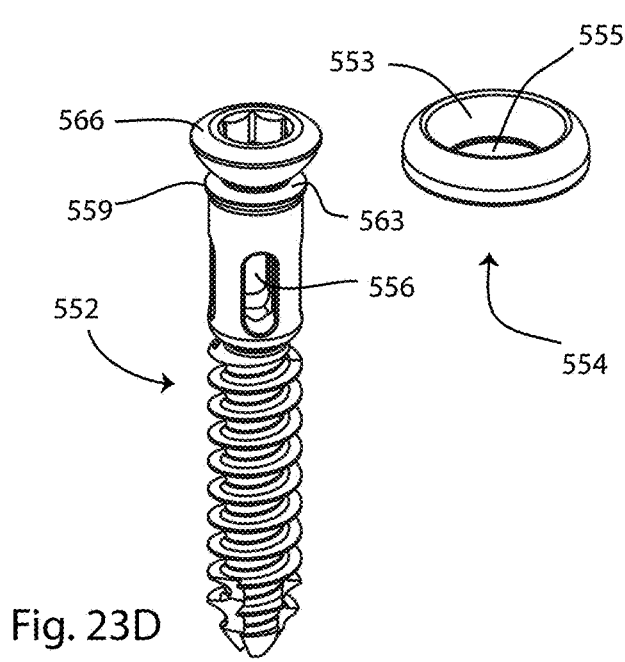
FIG. 23D is an exploded view of the fusion device of FIG. 1.
Figure 39:
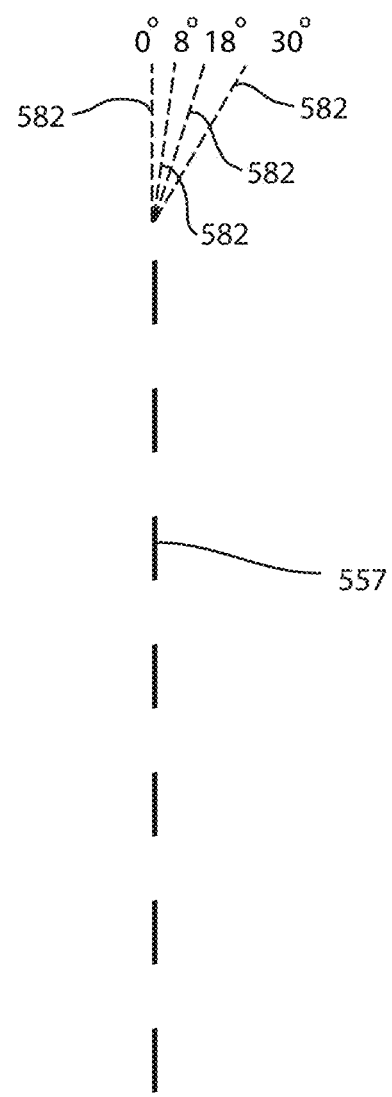
FIG. 39 depicts a longitudinal axis of the screw member of FIG. 1, and a washer bore central axis of the washer of FIG. 1 at various degrees of angulation with respect to the screw member longitudinal axis.

FIG. 39 depicts the relationship of the central bore axis 582 of the washer bore 555 relative to the longitudinal axis 557 of the screw member at various degrees of angulation. In the neutral position, for example as seen in FIGS. 23A and 23C, the washer bore axis 582 is coaxial with the screw member axis 557, and the washer member is angled at 0 degrees relative to the screw member. In an embodiment, the washer/screw connection permits at least +/−8 degrees of angulation of the washer member relative to the screw member. In other embodiments, the washer/screw connection permits +/−9 degrees, +/−10 degrees, +/−11 degrees, +/−12 degrees, +/−13 degrees, +/−14 degrees, +/−15 degrees, +/−16 degrees, +/−17 degrees, +/−18 degrees, +/−19 degrees, +/−20 degrees, +/−21 degrees, +/−22 degrees, +/−23 degrees, +/−24 degrees, +/−25 degrees, +/−26 degrees, +/−27 degrees, +/−28 degrees, +/−29 degrees, or +/−30 degrees of angulation of the washer member relative to the screw member.

The implant 550 may include one or more surface finishes to promote engagement with bone. The lag zone 560 and/or the threaded engagement zone 558 may be grit-blasted and/or include a hydroxyapatite coating or a non-hydroxyapatite coating to provide a roughened surface finish. The screw member tip 568 may have a non-roughened surface finish for easier insertion into bone. The screw head 566 and washer capsule 553 may each have a non-roughened surface finish to permit easy angulation of the washer with respect to the screw head. For example, in an embodiment, the screw head 566 and body 564 distal to and including the lip 559 may be glass bead finished or polished to provide the non-roughened finish; the body 564 distal of the lip 559 to the tip 568 may be titanium anodized, and optionally coated with hydroxyapatite coating, to provide the roughened surface finish; and the tip may be glass bead blasted or polished to produce the non-roughened surface finish.

Figure 21:
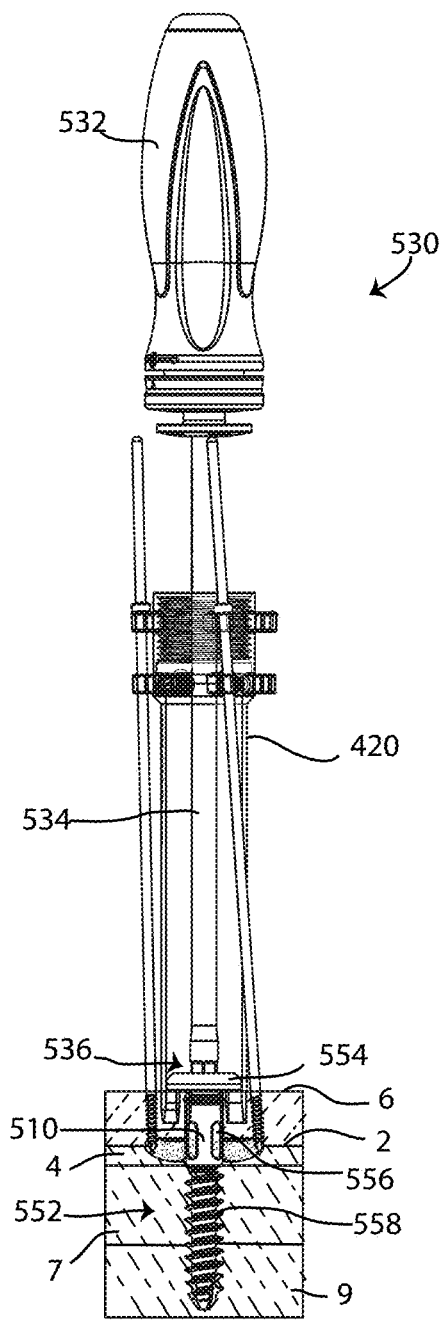

In a method of implantation, an implant inserter 530 may be used in a step to place and engage the fusion implant 550 in the prepared site, as shown in FIG. 21. The inserter 530 includes a handle portion 532, a shaft portion 534 and an engagement tip 536. Some or all of the inserter 530 may be cannulated. The engagement tip 536 may include features to engage with the engagement features 567 of the head 566 to enable insertion and rotation of the screw member 552. The inserter 530 may further include a ratchet system or other mechanisms for implant rotation or deployment. In a method of use, the screw member 552 may be coupled with the washer member 554, with the head 566 received in the washer capsule 553 and the screw body 564 protruding distally. The implant 550 may be placed over the proximal end 401 of the guide wire 400, with the screw member tip 568 extending distally toward the joint or procedure site. The inserter engagement tip 536 is coupled to the implant 550, and the inserter may be moved to urge the implant 550 distally along the guide wire 400 toward the prepared site. As the implant 550 crosses the joint 2 and the cavity 20 and into passageway 28, the threaded engagement zone 558 may engage in the sacrum 5. The tip 568 and a portion of the engagement zone 558 may be embedded in the sacral vertebral body 9, which has a higher bone density than the sacral ala and may therefore provide better long-term biological fixation. The inserter 530 may be rotated or otherwise deployed to rotate the implant 550 and secure it in the bone. Once the washer member 554 abuts the ilium 6, the implant 550 may be further rotated to provide compressive force across the joint 2. The washer member 554 may be angled relative to the screw member 552 to permit maximum surface contact of the distal side of the washer member with the ilium. The fusion zone 565 extends from the exterior ilium bone surface, through the ilium, and through the cavity and joint, and may contact the sacrum. In the fully inserted and secured position such as shown in FIGS. 1, 21 and 22, the apertures 556 are aligned with and open to the joint 2 and the cavity 20, allowing for graft distribution into and through the implant 550, and bone through-growth.

Figure 22:
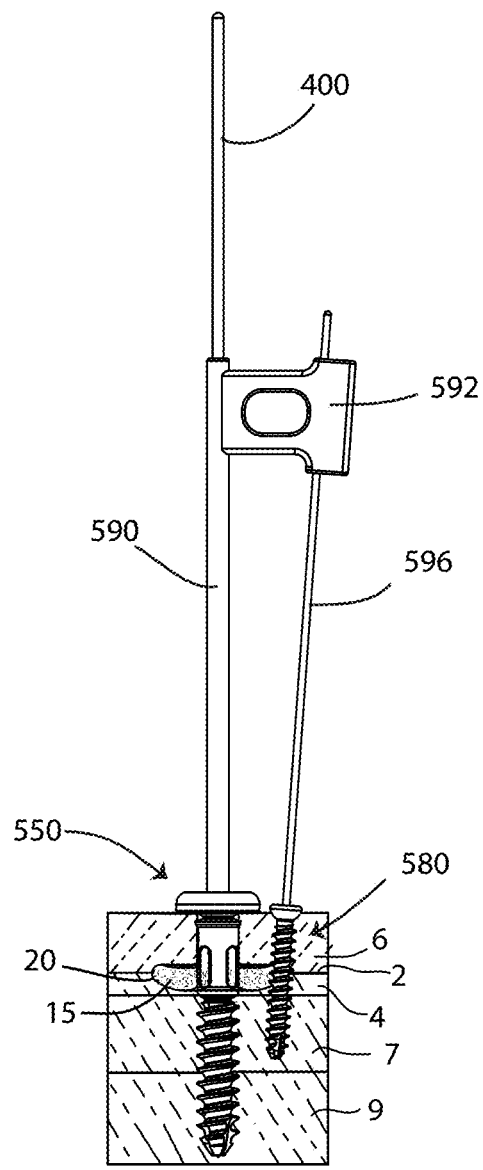

With regard to FIG. 22, in another step of the method a secondary or auxiliary screw 580 may be deployed to extend across the joint 2 to further stabilize the joint. Auxiliary screw 580 may be fully threaded and self-tapping. A guide brace 590 may be mounted over guide wire 400 to assist in determining a trajectory for auxiliary screw 580. The guide brace 590 includes a bracket 592, which may be angled. A guide wire 596 is guided through the bracket 592 and into the procedure site, at an oblique angle relative to the longitudinal axis of the implant 550 and guide wire 400. The auxiliary screw 580 is introduced over guide wire 596 along the trajectory and through the ilium 6 and into the sacrum 5, crossing the joint 2. In another embodiment of the method, more than one fusion implant 550 may be implanted. In other embodiments of the method, no auxiliary screw 580 may be deployed, or multiple auxiliary screws may be deployed. In other embodiments of the method, an auxiliary screw 580 may be implanted to extend parallel to the primary fusion implant 550, and a guide brace with a parallel bracket may be used.

FIGS. 29-37 disclose alternate embodiments of fastener members which may be included in a fusion implant such as implant 550. Any of the fastener members may be coupled with washer member 554 to form a fusion implant, or may be combined with other washer members, or may be used individually. Any of the fastener members disclosed herein may include surface roughening, grit-blasting, or coatings on all or a portion of the fastener member to promote bone engagement. Any of the fastener members may be cannulated, and may include fenestrations or windows for graft distribution or bone ingrowth.

Referring to FIGS. 29-33, alternate embodiments of screw-type fastener members are disclosed. Fastener member 600 includes head 602, tip 603, threaded portion 604, lag portion 606, and annular grooves 608. Fastener member 600 is a combination fastener, the threaded portion 604 having a double lead tip transitioning to a single lead toward the head 602. The thread diameter of the threaded portion 604 may taper moving from the lag portion 606 toward the tip 603. Fastener member 610 includes head 612, tip 613, threaded portion 614, lag portion 616, and annular grooves 618. Fastener member 610 is a double lead screw with dual threads of increasing height moving from the tip 613 toward the head 612. Fastener member 620 includes head 622, tip 623, threaded portion 624, lag portion 626, and annular grooves 628. Fastener member 620 is a single lead screw having tall threads to support cancellous bone. Fastener member 630 includes head 632, tip 633, threaded portion 634, lag portion 636, and annular grooves 638. Fastener member 630 is a double lead screw having dual height threads which provide additional joint compression when the member 630 is implanted across a joint. Fastener member 640 includes head 642, tip 643, threaded portion 644, lag portion 646, and annular grooves 648. Fastener member 640 includes double lead threading which may allow faster installation than fasteners with single lead threading. The annular grooves 608, 618, 628, 638, 648 are tapered towards the respective fastener head to provide resistance to fastener withdrawal. The annular grooves may also function as compression bands to grab bone and provide added compression across a joint as they are driven into bone. The lag portions 606, 616, 626, 636, 646 may be proportioned to accommodate the width of a bone they are implanted in, such as an ilium.

Referring to FIGS. 34-37, alternate embodiments of nail-type fastener members are disclosed. Fastener members 650, 660, 670 and 680 may be used as supplementary or auxiliary implant to a fusion device such as 550, to provide additional compression across a joint, and resistance to joint rotation. Fastener member 650 includes a head 652 and tip 654 with spiral shaft 656 extending therebetween. The spiral shaft 656 includes a fast hexagonal spiral which provides compression across the joint. Fastener member 660 includes a head 662 and tip 664 with spiral shaft 666 extending therebetween. The spiral shaft 666 includes a slow hexagonal spiral which provides compression across the joint. Fastener member 670 includes a head 672 and tip 674 with spiral shaft 676 extending therebetween. The spiral shaft 676 includes a slow square spiral which provides compression across the joint. Fastener member 680 includes a head 682 and tip 684 with shaft 686 extending therebetween. The shaft 686 comprises annular grooves which taper toward the head 682, and which provide compression across the joint and resistance to withdrawal.

The present invention may be embodied in other specific forms without departing from its spirit or essential characteristics. Above are described various alternative examples of systems and methods for joint fusion and for creating a cavity within a bone or joint. It is appreciated that various features of the above-described examples can be mixed and matched to form a variety of other combinations and alternatives. Not every instrument described herein may be used in a procedure such as a joint fusion. For example, in a method of fusing a joint, the steps of using the cutter instrument may be optional. In other embodiments of the method, the sleeve and/or cannula may be optional. The instruments described herein may be used in other procedures not described herein. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method for compressing a joint between a first bone portion and a second bone portion, wherein a cavity is located within the joint between the first bone portion and the second bone portion, the method comprising:
   positioning an implant proximate the joint, the implant comprising a screw member having a screw head and a screw body projecting distally from the screw head along a longitudinal axis to a screw distal end, the screw body comprising a non-threaded lag zone and a threaded engagement zone; and a washer member having a proximal side and a distal side, wherein the screw head is received in the washer member; wherein the implant further comprises a fusion zone having a length which is measured from the distal side of the washer member to a proximal end of the screw engagement zone, wherein the length of the implant fusion zone ranges from about 10 mm to about 37 mm;
   inserting the screw body engagement zone through the first bone portion and into the cavity;
   engaging the screw body engagement zone with the second bone portion;
   positioning at least a portion of the lag zone within the cavity;
   rotating the screw member to compress the joint; and
   angling the washer member with respect to the screw member to permit maximum surface contact of the distal side of the washer member with the first bone portion.

2. The method of claim 1, wherein the lag zone comprises a fenestration opening into a central longitudinal bore, wherein the method further comprises: filling the fenestration with bone graft material.

3. The method of claim 1, further comprising: filling the cavity with bone graft material.

4. The method of claim 1, wherein the washer member comprises a bore having a central bore axis; wherein angling the washer member with respect to the screw member comprises angling the washer member central bore axis with respect to the screw member longitudinal axis within the range of at least −8 degrees to at least +8 degrees.

5. The method of claim 1, wherein the implant is a sacro-ilial fusion implant and the joint is a sacro-iliac joint, and wherein the first bone portion is an ilium, and the second bone portion is a sacrum, and the cavity is located between the ilium and the sacrum.

6. The method of claim 1, further comprising: positioning the fusion zone to extend into the cavity, wherein the fusion zone crosses the first bone portion and extends into the cavity.

7. The method of claim 6, further comprising:
  positioning the fusion zone to contact the second bone portion.

* * * * *